(12) United States Patent
Makino et al.

(10) Patent No.: US 12,376,774 B2
(45) Date of Patent: Aug. 5, 2025

(54) INFORMATION PROCESSING SYSTEM, INFORMATION PROCESSING METHOD, AND INFORMATION PROCESSING APPARATUS BASED ON AUDIENCE EMOTION FOR AUDIENCE PLACEMENT

(71) Applicant: FUJIFILM Corporation, Tokyo (JP)

(72) Inventors: Kenji Makino, Saitama (JP); Masahiro Terada, Saitama (JP); Daisuke Hayashi, Saitama (JP); Shunta Ego, Saitama (JP)

(73) Assignee: FUJIFILM Corporation, Tokyo (JP)

( * ) Notice: Subject to any disclaimer, the term of this patent is extended or adjusted under 35 U.S.C. 154(b) by 621 days.

(21) Appl. No.: 17/688,825

(22) Filed: Mar. 7, 2022

(65) Prior Publication Data

US 2022/0192561 A1 Jun. 23, 2022

Related U.S. Application Data

(63) Continuation of application No. PCT/JP2020/035898, filed on Sep. 24, 2020.

(30) Foreign Application Priority Data

Sep. 26, 2019 (JP) .................. 2019-175713

(51) Int. Cl.
*A61B 5/16* (2006.01)
*A61B 5/00* (2006.01)
(Continued)

(52) U.S. Cl.
CPC ............ *A61B 5/165* (2013.01); *A61B 5/0077* (2013.01); *A61B 5/4803* (2013.01);
(Continued)

(58) Field of Classification Search
CPC ..... A61B 5/165; A61B 5/0077; A61B 5/4803; A61B 5/7267; A61B 2576/02;
(Continued)

(56) References Cited

U.S. PATENT DOCUMENTS 10,547,902 B2 1/2020 Oobuchi et al.
10,863,939 B2 12/2020 Silawan et al.
(Continued)

FOREIGN PATENT DOCUMENTS

CN 106580346 4/2017
JP 2012519336 8/2012
(Continued)

OTHER PUBLICATIONS

Borges Fortes Neto et al., "Giving Emotional Contagion Ability to Virtual Agents in Crowds," 2017, Springer, Cham, Intelligent Virtual Agents (IVA) 2017, Lecture Notes in Computer Science(), vol. 10498. https://doi.org/10.1007/978-3-319-67401-8_7 (Year: 2017).*

(Continued)

*Primary Examiner* — Emily C Terrell
*Assistant Examiner* — Julia Z. Yao
(74) *Attorney, Agent, or Firm* — JCIPRNET

(57) ABSTRACT

Provided are an information processing system, an information processing method, and an information processing apparatus that can grasp an emotion transmission ability. An index of emotion of a person in a first area is measured. Map data representing the measured index in association with a position of the person in the first area is created. An emotion transmission ability of the person is estimated based on the created map data. Information on the estimated emotion transmission ability of the person is stored in a storage unit.

21 Claims, 19 Drawing Sheets

(51) Int. Cl.
*G06Q 30/0201* (2023.01)
*G06V 40/16* (2022.01)
*G10L 25/63* (2013.01)

(52) U.S. Cl.
CPC ....... *A61B 5/7267* (2013.01); *G06Q 30/0201* (2013.01); *G06V 40/166* (2022.01); *G06V 40/175* (2022.01); *G10L 25/63* (2013.01); *A61B 2576/02* (2013.01)

(58) Field of Classification Search
CPC .... G06Q 30/0201; G06Q 10/02; G06Q 10/04; G06Q 50/10; G06Q 10/025; G06Q 10/043; G06V 40/166; G06V 40/175; G06V 40/15; G06V 40/161; G06V 40/174; G10L 25/63; G09B 19/00; G06F 2203/011; G01H 2230/085; G06T 2207/30201
See application file for complete search history.

(56) References Cited

U.S. PATENT DOCUMENTS

| | | | |
|---|---|---|---|
| 11,265,603 B2 | 3/2022 | Oobuchi et al. | |
| 2015/0049953 A1* | 2/2015 | Movellan | G06V 10/945 382/197 |
| 2016/0170996 A1* | 6/2016 | Frank | G06F 16/904 707/748 |
| 2019/0213423 A1* | 7/2019 | Haberstroh | H04N 21/41407 |
| 2019/0259066 A1 | 8/2019 | Asukai | |
| 2020/0387934 A1* | 12/2020 | M V | G06Q 30/0271 |
| 2021/0158228 A1* | 5/2021 | Shimizu | G06V 40/70 |
| 2021/0158781 A1* | 5/2021 | Imamura | H04N 21/422 |

FOREIGN PATENT DOCUMENTS

| | | | |
|---|---|---|---|
| JP | 2014006742 | | 1/2014 |
| JP | 2016133939 | | 7/2016 |
| JP | 2017182767 A | * | 10/2017 |
| JP | 2017211932 | | 11/2017 |
| JP | 2018190318 | | 11/2018 |
| JP | 2019028485 | | 2/2019 |
| WO | 2010099632 | | 9/2010 |
| WO | 2016009865 | | 1/2016 |
| WO | WO-2016178329 A1 | * | 11/2016 ............... G06F 3/01 |
| WO | 2018087968 | | 5/2018 |
| WO | 2018207619 | | 11/2018 |

OTHER PUBLICATIONS

Bosse et al. Agent-Based Modeling of Emotion Contagion in Groups. Cogn Comput 7, 111-136 (2015). https://doi.org/10.1007/s12559-014-9277-9 (Year: 2015).*
Navarathna et al., "Estimating Audience Engagement to Predict Movie Ratings," in IEEE Transactions on Affective Computing, vol. 10, No. 1, pp. 48-59, Jan. 1-Mar. 2019, doi: 10.1109/TAFFC.2017.2723011. (Year: 2019).*
Durupınar et al., "Psychological Parameters for Crowd Simulation: From Audiences to Mobs," in IEEE Transactions on Visualization and Computer Graphics, vol. 22, No. 9, pp. 2145-2159, Sep. 1, 2016, doi: 10.1109/TVCG.2015.2501801. (Year: 2016).*
Mao et al., "Modeling Group Structures With Emotion in Crowd Evacuation," in IEEE Access, vol. 7, pp. 140010-140021, 2019, doi: 10.1109/ACCESS.2019.2943603. (Year: 2019).*
Xiang et al. Using SIR Model to Simulate Emotion Contagion in Dynamic Crowd Aggregation Process [J]. Int J Performability Eng, 2018, 14(1): 134-143. (Year: 2018).*
Office Action of Japan Counterpart Application, with English translation thereof, issued on Aug. 26, 2022, pp. 1-12.
"International Search Report (Form PCT/ISA/210) of PCT/JP2020/035898," mailed on Dec. 15, 2020, with English translation thereof, pp. 1-5.
"Written Opinion of the International Searching Authority (Form PCT/ISA/237)" of PCT/JP2020/035898, mailed on Dec. 15, 2020, with English translation thereof, pp. 1-7.
"Office Action of China Counterpart Application", with English translation thereof, issued on Nov. 28, 2024, pp. 1-11.

* cited by examiner

FIG. 12

| USER ID | EMOTION TRANSMISSION ABILITY | | | ATTRIBUTE INFORMATION | | |
|---|---|---|---|---|---|---|
| | LEADERSHIP | FOLLOWERSHIP | ... | AGE | GENDER | ... |
| AA0001 | 1 | 0.8 | ... | 30 | MALE | ... |
| AA0002 | 0 | 0.5 | ... | 24 | MALE | ... |
| AA0003 | 0 | 0.2 | ... | 53 | FEMALE | ... |
| AA0004 | 0 | 0.5 | ... | 35 | FEMALE | ... |
| ... | ... | ... | ... | ... | ... | ... |
| XX9999 | 1 | 0.9 | ... | 27 | MALE | ... |

INFORMATION PROCESSING SYSTEM, INFORMATION PROCESSING METHOD, AND INFORMATION PROCESSING APPARATUS BASED ON AUDIENCE EMOTION FOR AUDIENCE PLACEMENT

CROSS-REFERENCE TO RELATED APPLICATIONS

The present application is a Continuation of PCT International Application No. PCT/JP2020/035898 filed on Sep. 24, 2020 claiming priority under 35 U.S.C § 119(a) to Japanese Patent Application No. 2019-175713 filed on Sep. 26, 2019. Each of the above applications is hereby expressly incorporated by reference, in its entirety, into the present application.

BACKGROUND OF THE INVENTION

1. Field of the Invention

The present invention relates to an information processing system, an information processing method, and an information processing apparatus.

2. Description of the Related Art

JP2016-133939A discloses, as a performer information storage system, a system that images an audience who watches a play in a theater, calculates a value indicating a degree of a smile of the audience based on the obtained image data, and stores the calculated value in association with the performer of the play.

WO2016/009865A describes the technology of visualizing a degree of excitement of a user who watches a motion picture by a heat map and presenting the visualized degree of excitement to a performer or the like in a venue in a service for delivering the motion picture in real time, such as a concert.

SUMMARY OF THE INVENTION

One embodiment according to the technology of the present disclosure provides an information processing system, an information processing method, and an information processing apparatus that can grasp an emotion transmission ability.

(1) An information processing system comprising a measurement unit that measures an index of emotion of a person in a first area, a map data creation unit that creates map data representing the index measured by the measurement unit in association with a position of the person in the first area, an estimation unit that estimates an emotion transmission ability of the person based on the map data created by the map data creation unit, and a storage unit storing information on the emotion transmission ability of the person estimated by the estimation unit.

(2) The information processing system according to (1), in which the measurement unit includes an emotion measurement unit that measures emotion of the person in the first area, and a calculation unit that calculates the index of the person based on a measurement result of emotion of the person by the emotion measurement unit.

(3) The information processing system according to (2), in which, based on the measurement result by the emotion measurement unit, the calculation unit calculates at least one of a level of emotion or amplitude of emotion of the person, and calculate the index of the person.

(4) The information processing system according to (2) or (3), in which the measurement unit further includes an imaging unit that images the first area, and a face detection unit that detects a face of the person in the first area from an image captured by the imaging unit, in which the emotion measurement unit measures emotion of the person based on an image of the face of each person detected by the face detection unit.

(5) The information processing system according to any one of (2) to (4), in which the measurement unit further includes a biological information reception unit that receives biological information of the person in the first area, in which the calculation unit further calculates the index of the person based on the biological information of the person received by the biological information reception unit.

(6) The information processing system according to any one of (2) to (5), in which the measurement unit further includes a voice information reception unit that receives information on voice uttered by the person in the first area, in which the calculation unit further calculates the index of the person based on the information on the voice received by the voice information reception unit.

(7) The information processing system according to any one of (2) to (6), in which the measurement unit further includes a vibration information reception unit that receives information on vibration of the person in the first area, in which the calculation unit calculates the index of the person based on information of vibration of the person received by the vibration information reception unit.

(8) The information processing system according to any one of (1) to (7), in which the estimation unit estimates, as the emotion transmission ability, at least one of a first ability, which is an ability to give emotion to surroundings, or a second ability, which is an ability to accept emotion of surroundings.

(9) The information processing system according to (8), in which the estimation unit extracts a region in which the index is equal to or more than a threshold value from the map data, obtains a centroid of the extracted region, and estimates the first ability of the person.

(10) The information processing system according to (9), in which the estimation unit further calculates a sum of the indexes of the person in the region from the map data, and estimates a degree of the first ability of the person positioned at the centroid of the region.

(11) The information processing system according to (8), in which, based on the map data, the estimation unit obtains a sum of the indexes of the person positioned within a predetermined distance from the person for each person, and estimates a degree of the first ability of the person.

(12) The information processing system according to (8), in which the estimation unit estimates the second ability of the person based on the map data of a time series.

(13) The information processing system according to (12), in which the estimation unit obtains a propagation rate of the index from the map data of a time series, and estimates a degree of the second ability of the person.

(14) The information processing system according to any one of (1) to (13), further comprising an attribute information reception unit that receives attribute information of the person, in which the storage unit further stores the attribute information of the person received by the attribute information reception unit.

(15) The information processing system according to any one of (1) to (14), further comprising a person information reception unit that receives information on a person placed in a second area, an information acquisition unit that acquires information on the emotion transmission ability of the person placed in the second area from the storage unit, and a placement decision unit that decides placement of the person in the second area based on the information on the emotion transmission ability of the person placed in the second area.

(16) The information processing system according to (15), further comprising a discrimination unit that discriminates the emotion transmission ability of the person based on the information on the person, in which the discrimination unit discriminates the emotion transmission ability of the person whose information is not present in the storage unit.

(17) The information processing system according to (16), in which the discrimination unit discriminates the emotion transmission ability of the person by using a discrimination model generated by machine learning.

(18) The information processing system according to (17), in which the discrimination unit discriminates the emotion transmission ability of the person by using the discrimination model generated by machine learning using the information stored in the storage unit.

(19) The information processing system according to any one of (15) to (18), in which, based on the information on the emotion transmission ability of the person placed in the second area, the placement decision unit simulates a change of the index of the person placed in the second area, obtains placement in which the index is uniform and maximized within the second area, and decides the placement of the person in the second area.

(20) The information processing system according to (19), further comprising an extraction unit that extracts the person having a high emotion transmission ability from among the persons whose information is stored in the storage unit, in which the placement decision unit decides the placement of the person in the second area by adding the person extracted by the extraction unit.

(21) The information processing system according to any one of (15) to (20), further comprising a reception unit that receives a request for placement from the person placed in the second area, in which the placement decision unit further decides the placement of the person in the second area based on the request received by the reception unit.

(22) An information processing method comprising a step of measuring an index of emotion of a person in a first area, a step of creating map data representing the measured index in association with a position of the person in the first area, a step of estimating an emotion transmission ability of the person based on the created map data, and a step of storing information on the estimated emotion transmission ability of the person in a storage unit.

(23) The information processing method according to (22), further comprising a step of receiving information on a second area, a step of receiving information on a person placed in the second area, a step of acquiring information on the emotion transmission ability of the person placed in the second area from the storage unit, and a step of deciding placement of the person in the second area based on the information on the emotion transmission ability of the person placed in the second area.

(24) An information processing apparatus comprising a storage unit storing information on an emotion transmission ability of a person, a person information reception unit that receives information on a person placed in a second area, an information acquisition unit that acquires information on the emotion transmission ability of the person placed in the second area from the storage unit, and a placement decision unit that decides placement of the person in the second area based on the information on the emotion transmission ability of the person placed in the second area.

BRIEF DESCRIPTION OF THE DRAWINGS

FIG. 12 is a diagram showing an example of a customer database.

DESCRIPTION OF THE PREFERRED EMBODIMENTS

In the following, preferred embodiments of the present invention will be described in detail with reference to the accompanying drawings.

First Embodiment

In a case of viewing or watching an event, such as a concert or sports (whether paid or free), the surrounding atmosphere (surrounding excitement or the like) has a large influence on the satisfaction of each audience. Therefore, in order to improve the satisfaction of each audience, it is preferable to place each audience in consideration of an emotion transmission ability of each audience (an ability to give emotion to surroundings, an ability to accept emotion of surroundings, and the like). That is, it is preferable to place each audience such that the excitement in the entire venue can be obtained evenly. However, in the related art, there is no way to grasp the emotion transmission ability of each audience. For this reason, in a case in which the event is held, it is not possible to place the audience to maximize the satisfaction of the audience.

In the present embodiment, emotion of the audience who views the event is measured, and the emotion transmission ability of each audience is estimated based on a measurement result. In addition, the estimated emotion transmission ability of each audience is made into a database. Further, the database will be used to decide the placement of the audience for future events.

System Configuration

Figure 1:
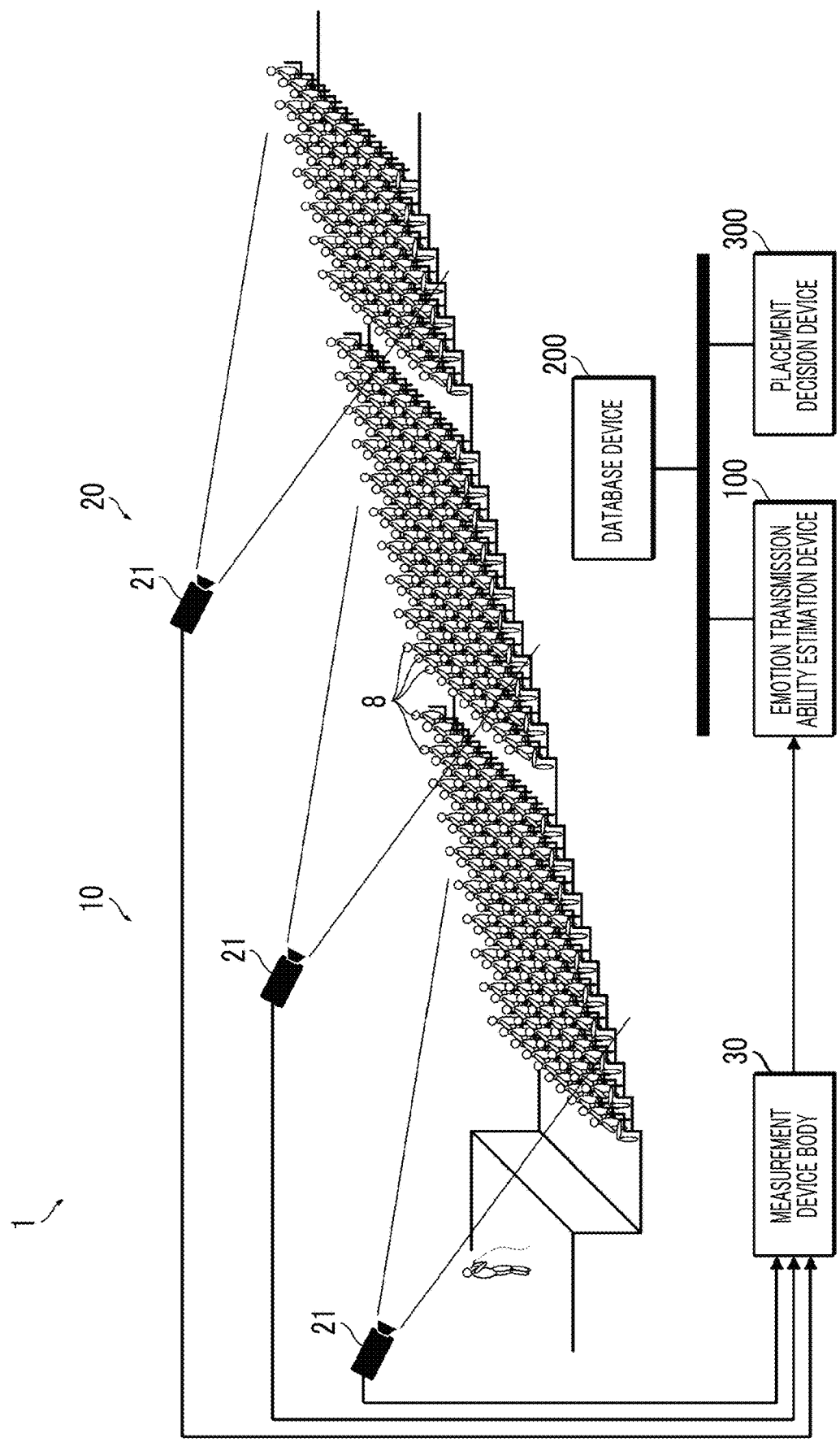
FIG. 1 is a diagram showing a schematic configuration of an information processing system.

FIG. 1 is a diagram showing a schematic configuration of an information processing system according to the present embodiment.

As shown in FIG. 1, an information processing system 1 according to the present embodiment mainly comprises an emotion amount measurement device 10, an emotion transmission ability estimation device 100, a database device 200, a placement decision device 300, and the like.

Emotion Amount Measurement Device

The emotion amount measurement device 10 measures the emotion amount of the audience (person) who views the event, watches the sports, or the like. The emotion amount measurement device 10 is an example of a measurement unit. The emotion amount is a numerical value indicating a state of emotion (joy, anger, grief, pleasure, and the like) (level of emotion, such as joy, anger, grief, and pleasure, magnitude of amplitude of emotion, and the like). The emotion amount is an example of an index indicating emotion of the person.

Figure 2:
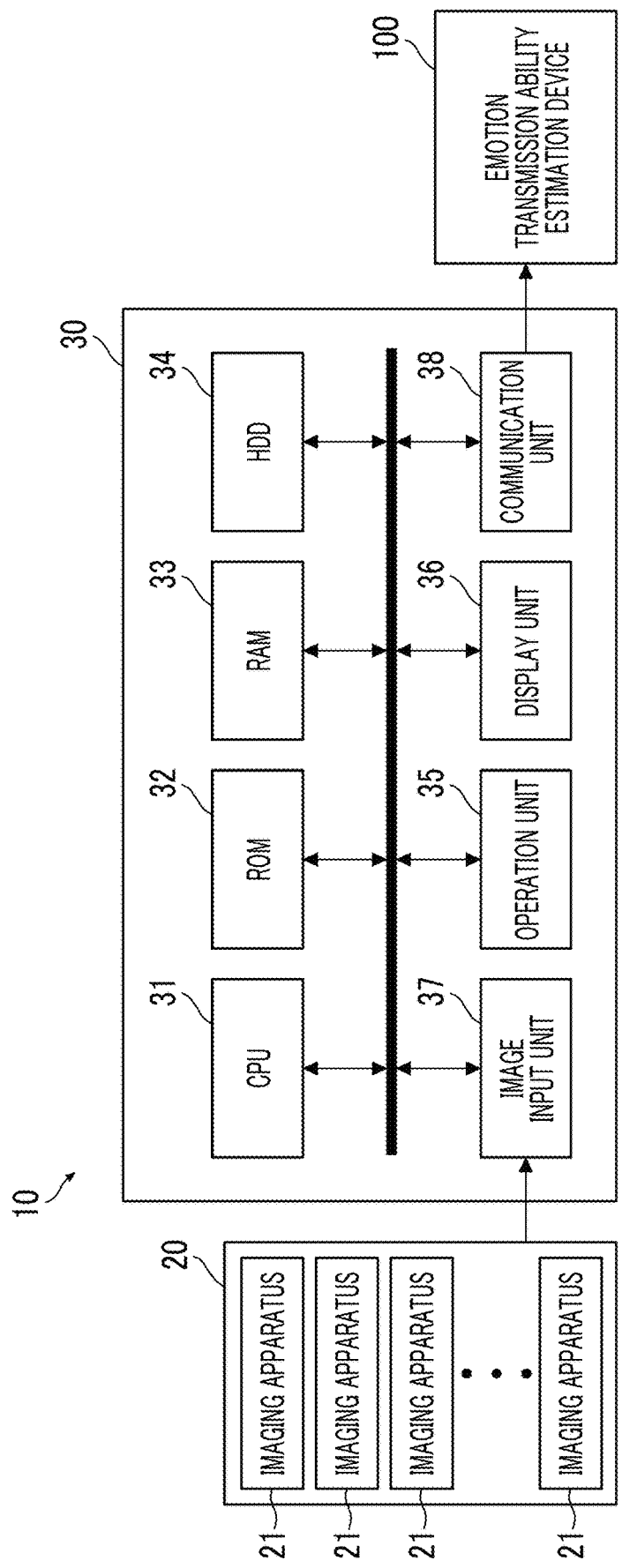
FIG. 2 is a diagram showing a schematic configuration of an emotion amount measurement device.

FIG. 2 is a diagram showing a schematic configuration of the emotion amount measurement device. The emotion amount measurement device 10 includes an imaging unit 20 that images an audience 8 and a measurement device body 30 that processes the image captured by the imaging unit 20 and measures the emotion amount of each audience.

The imaging unit 20 images an area (first area) in which the audience is present in the venue in which the event is held. Specifically, the area of the audience seats is imaged, and the audience 8 who views the event or watches the sports in the audience seat (seat) is imaged (see FIG. 1).

The imaging unit 20 is configured by at least one imaging apparatus 21. In a case in which one imaging apparatus 21 can image all (including almost all) areas, the imaging unit 20 is configured by one imaging apparatus 21. For example, in a case in which one imaging apparatus 21 can image all the audiences 8 in a target area by using a wide-angle lens or the like, the imaging unit 20 is configured by one imaging apparatus 21. On the other hand, in a case in which one imaging apparatus 21 cannot image all the audiences 8 in the area, the imaging unit 20 is configured by a plurality of the imaging apparatuses 21. In this case, the target area is divided into a plurality of areas, and the divided areas are shared and imaged by the plurality of imaging apparatuses 21.

The imaging apparatus 21 captures an image having an image quality capable of discriminating at least an expression of the audience 8. Therefore, it is preferable to use an imaging apparatus having a high resolution as the imaging apparatus 21. The imaging apparatus 21 is installed at a position at which a face of the audience 8 in the area, which is an imaging target, can be imaged.

The imaging apparatus 21 is configured by a so-called video camera (a digital still camera or the like having a function of capturing a motion picture (time series image) is assembled). The image (time series image) captured by the imaging apparatus 21 is output to the measurement device body 30.

The measurement device body 30 is configured by a computer comprising a central processing unit (CPU) 31, a read only memory (ROM) 32, a random access memory (RAM) 33, a hard disk drive (HDD) 34, an operation unit (for example, a keyboard, a mouse, or a touch panel) 35, a display unit (for example, a liquid crystal display) 36, an image input unit 37, a communication unit 38, and the like. The measurement device body 30 is connected to each imaging apparatus 21 via the image input unit 37, and image data is input from each imaging apparatus 21. A connection form between the measurement device body 30 and each imaging apparatus 21 may be wired or wireless. In addition, the measurement device body 30 is communicably connected to the emotion transmission ability estimation device 100 and the like via the communication unit 38. A connection form between the measurement device body 30 and the emotion transmission ability estimation device 100 may be wired or wireless.

Figure 3:
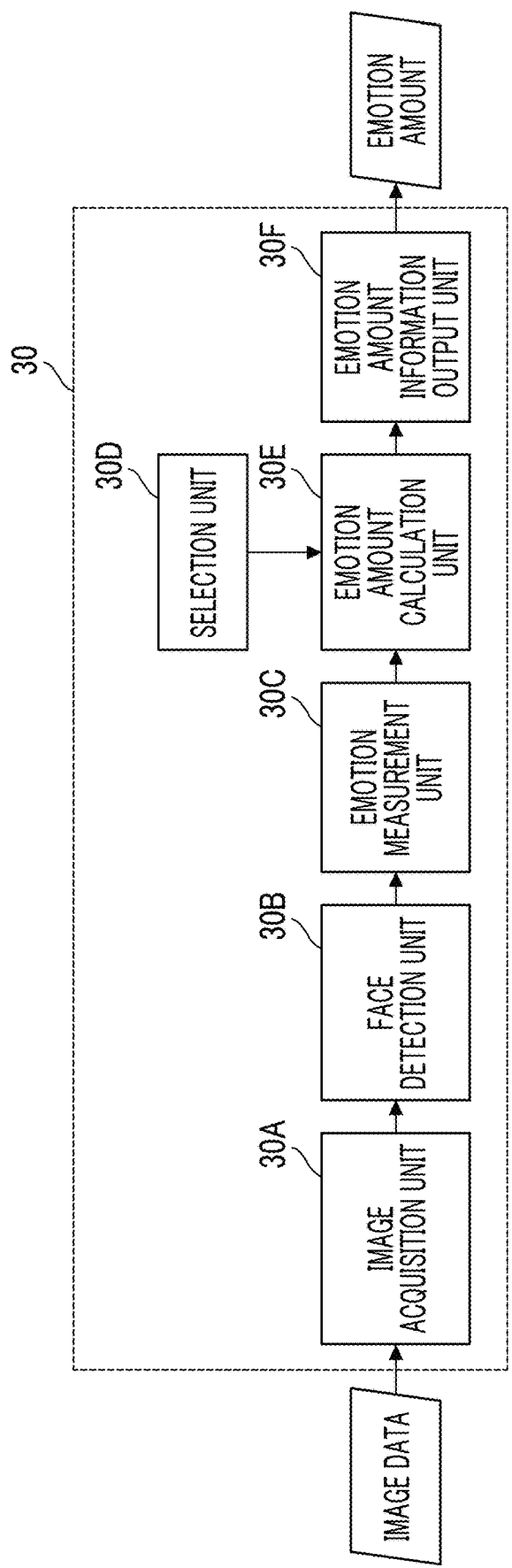
FIG. 3 is a block diagram of a function of a measurement device body.

FIG. 3 is a block diagram of a function of the measurement device body.

As shown in FIG. 3, the measurement device body 30 has functions of an image acquisition unit 30A, a face detection unit 30B, an emotion measurement unit 30C, a selection unit 30D, an emotion amount calculation unit 30E, and an emotion amount information output unit 30F. These functions are realized by executing a predetermined program by the CPU 31 as a processor. This program is stored, for example, in the HDD 34.

The image acquisition unit 30A acquires the image (motion picture) obtained by imaging the audience 8 from the imaging apparatus 21 configuring the imaging unit 20 via the image input unit 37.

The face detection unit 30B detects the face of the audience from the acquired image. The face detection unit 30B detects the faces of all the audiences in the target area. A known method is adopted for the face detection.

The emotion measurement unit 30C measures emotion of the audience based on the image of the face of the audience detected by the face detection unit 30B. A type of emotion is represented by a word that indicates the emotion. Therefore, the measurement of the emotion means to specify the type of emotion by the word indicating the emotion. Specifying emotion may be specifying by a single word indicating the emotion or specifying by a combination of the words indicating the emotion. In a case in which words that indicate the emotion are combined, the words that indicate each emotion may be weighted. In the present embodiment, emotion is classified into four types (so-called joy, anger, grief, and pleasure) of "joy", "anger", "grief", and "pleasure". As the measurement result of the emotion, a score (emotion score) obtained by quantifying a degree of each emotion (also referred to as an emotional degree) is output. The emotion score is output with the maximum value set to 100, for example. The emotion score may be output such that the sum of the respective degrees of the emotion is 100. The emotion measurement unit 30C measures emotion of the audience by the image recognition. The image recognition can be performed by using, for example, an image recognition model generated by machine learning (for example, deep learning or the like). In addition, the emotion can be measured from the image of the face by using a known method.

The selection unit 30D receives the selection of a target to be calculated as the emotion amount. The target to be calculated as the emotion amount is a level (magnitude) of specific emotion or amplitude of the emotion. The target to be calculated as the emotion amount is selected depending on a content of the event. For example, in the concert, the magnitude of joy and pleasure is considered to lead to the satisfaction of the audience. Therefore, in a case of the concert, the levels of emotion of joy and pleasure are selected as the target to be calculated as the emotion amount. In addition, for example, in watching the sports, it is considered that the magnitude of the amplitude of the emotion (for example, the magnitude of the amplitude of the emotion of joy and grief) leads to the satisfaction of the audience. Therefore, in a case of watching the sports, the magnitude of the amplitude of emotion is selected as the target to be calculated as the emotion amount. The selection unit 30D receives the selection of the target via the operation unit 35.

The emotion amount calculation unit 30E calculates the target selected by the selection unit 30D as the emotion amount based on the measurement result of emotion of the audience by the emotion measurement unit 30C. Therefore, for example, in a case in which the selection unit 30D selects calculation of the level of the specific emotion as the emotion amount, the emotion amount calculation unit 30E calculates the level of the specific emotion as the emotion amount. In this case, the score of the selected emotion is calculated as the emotion amount. For example, in a case in which it is selected to calculate the level of emotion of joy as the emotion amount, the score of joy is calculated as the emotion amount. In addition, for example, in a case in which it is selected to calculate the levels of emotion of joy and pleasure as the emotion amount, the sum of the scores of joy and pleasure is calculated as the emotion amount. It should be noted that in a case in which the emotion amount is calculated as the sum of the scores of emotion, it may be calculated by weighting. That is, a configuration may be adopted in which the sum (emotion amount) is calculated by multiplying the score of each emotion by a predetermined coefficient. In addition, the selection unit 30D selects calculation of the amplitude of the specific emotion as the emotion amount, the emotion amount calculation unit 30E calculates the amplitude of the specific emotion as the emotion amount. For example, in a case in which it is selected to calculate the magnitude of the amplitude of emotion of joy and grief as the emotion amount, the emotion amount (magnitude of the amplitude of emotion) is calculated by calculating a difference between the score of joy and the score of grief (for example, difference between the score of joy at a time point t and the score of grief at a time point t+Δt) at predetermined time intervals. In addition, for example, in a case in which it is selected to calculate the magnitude of the amplitude of emotion of joy as the emotion amount, the emotion amount (magnitude of the amplitude of emotion) is calculated by calculating the difference between the scores of j oy at predetermined time intervals. The emotion amount calculation unit 30E is an example of a calculation unit.

The emotion amount information output unit 30F outputs (transmits) information on the emotion amount of each audience calculated by the emotion amount calculation unit 30E to the emotion transmission ability estimation device 100. The emotion amount information output unit 30F outputs (transmits) the information on the emotion amount of each audience to the emotion transmission ability estimation device 100 via the communication unit 38. In this case, the emotion amount information output unit 30F outputs the information on the emotion amount of each audience in association with the information on the position of each audience. The position of each audience is specified, for example, by a seat position. Information on the seat position (information on the venue) is acquired in advance. The acquired information on the seat position is stored in, for example, the HDD 34.

As described above, the emotion amount measurement device 10 measures the emotion amount of each audience based on the image obtained from the imaging unit 20. Since the images of the audience are continuously captured by the imaging unit 20, the emotion amount of each audience is continuously measured. It should be noted that the measurement does not necessarily have to be performed in all frames, and a configuration can be adopted in which the measurement is performed at predetermined frame intervals (time intervals). In addition, since it is not always possible to detect the faces of all the audiences at each timing (frame), the emotion amount is measured only for the audience whose face is detected. For the audience whose emotion amount cannot be measured, information indicating that the measurement cannot be performed is output.

Emotion Transmission Ability Estimation Device

The emotion transmission ability estimation device 100 estimates the emotion transmission ability of each audience based on the information on the emotion amount of each audience measured by the emotion amount measurement device 10.

The emotion transmission ability is expressed by at least one of an ability to give emotion to surroundings or an ability to accept emotion of surroundings.

The ability to give emotion to surroundings is the ability to give spontaneous emotion to surroundings. It is possible to regard this ability as the ability to spontaneously excite the atmosphere of the place (transmission ability). That is, it can be said that it is the ability to show the nature as a leader who excites the atmosphere of the place or an influencer who has a great influence on surroundings. The high degree of ability indicates the high degree of ability and influence as the leader or the influencer.

On the other hand, the ability to accept emotion of surroundings is the ability to easily accept emotion of surroundings. Therefore, a person with high ability is a person who is easily influenced by the emotion of surroundings. It is possible to regard this ability as the ability to follow the atmosphere of the place (following ability). That is, it can be said that it is the ability to show the nature of a follower who follows the leader. Therefore, it can be said that a person who has a high ability to accept emotion of surroundings is a person who has a high ability to excite depending on the atmosphere of the place. That is, it can be said that he is a person who has a high ability to react to the excitement of surroundings and to excite together.

The emotion transmission ability estimation device 100 according to the present embodiment estimates both abilities of the ability to give emotion to surroundings as "leadership" and the ability to accept emotion of surroundings as "followership". The leadership is an example of a first ability, and the followership is an example of a second ability.

The emotion transmission ability estimation device 100 creates a heat map based on the information on the emotion amount of each audience measured by the emotion amount measurement device 10, and estimates the emotion transmission ability (leadership and followership) based on the created heat map. The heat map is an example of map data.

Figure 4:
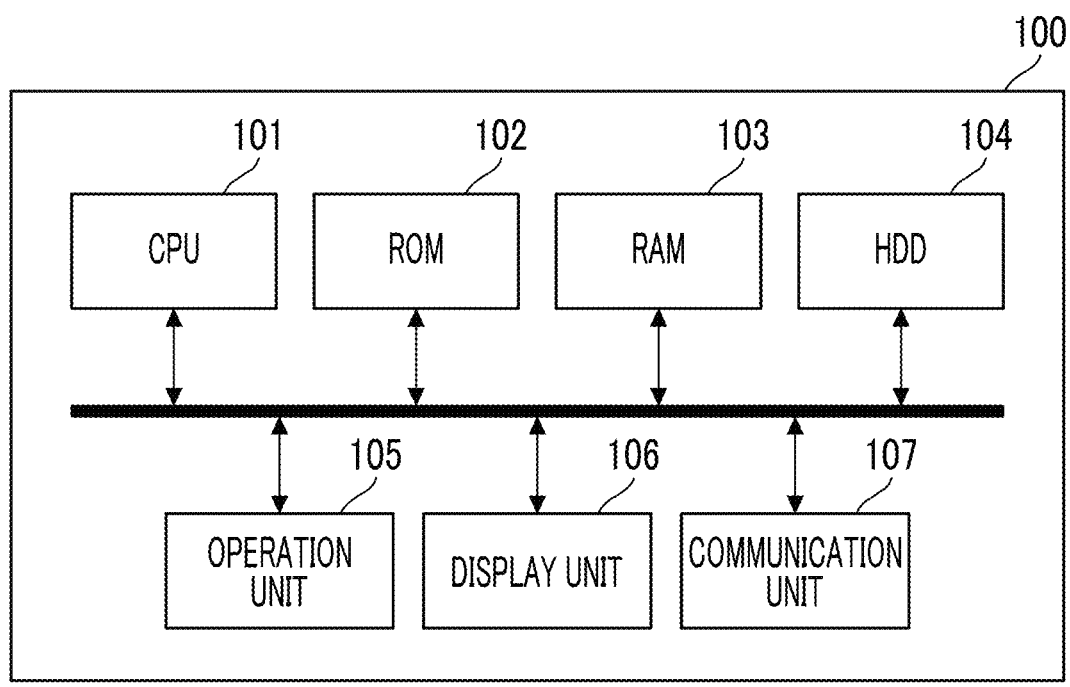
FIG. 4 is a block diagram showing an example of a hardware configuration of an emotion transmission ability estimation device.

FIG. 4 is a block diagram showing an example of a hardware configuration of the emotion transmission ability estimation device.

The emotion transmission ability estimation device 100 is configured by a computer comprising a CPU 101, a ROM 102, a RAM 103, an HDD 104, an operation unit (for example, a keyboard, a mouse, or a touch panel) 105, a display unit (for example, a liquid crystal display) 106, a communication unit 107, and the like. The emotion transmission ability estimation device 100 is communicably connected to the emotion amount measurement device 10, the database device 200, the placement decision device 300, and the like via the communication unit 107. A connection form thereof may be wired or wireless.

Figure 5:
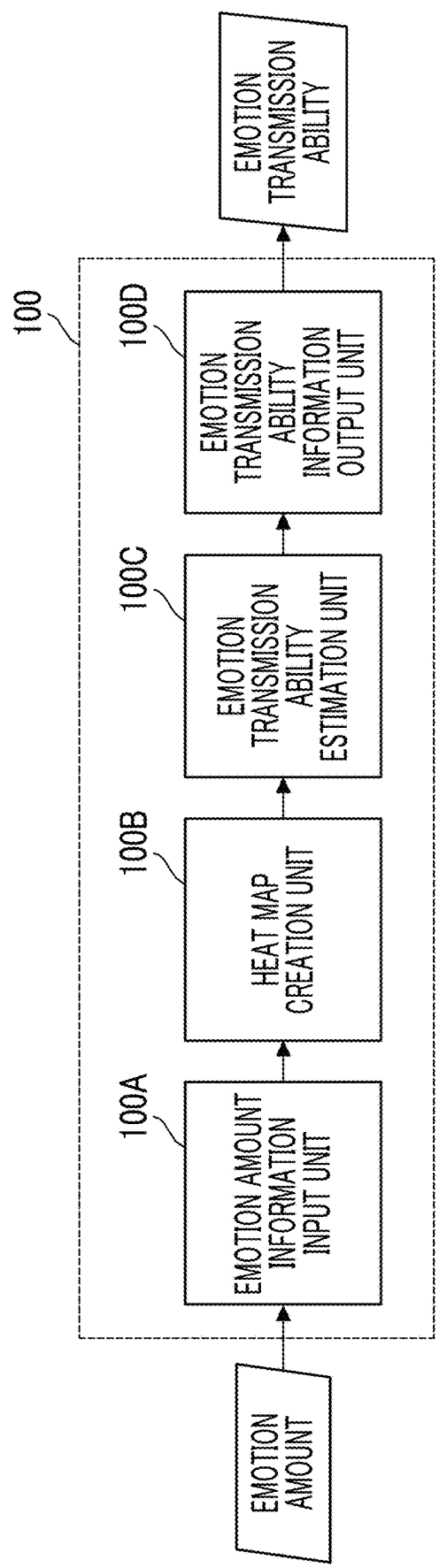
FIG. 5 is a block diagram of a function of the emotion transmission ability estimation device.

FIG. 5 is a block diagram of a function of the emotion transmission ability estimation device.

As shown in FIG. 5, the emotion transmission ability estimation device 100 has the functions of an emotion amount information input unit 100A, a heat map creation unit 100B, an emotion transmission ability estimation unit 100C, and an emotion transmission ability information output unit 100D. These functions are realized by executing a predetermined program by the CPU 101. This program is stored, for example, in the HDD 104.

The emotion amount information input unit 100A receives the input of the information on the emotion amount of each audience output (transmitted) from the emotion amount measurement device 10. The emotion amount information is input to (received by) the emotion amount information input unit 100A via the communication unit 107. The information on the emotion amount of each audience is input in association with the information on the position (seat position) of each audience.

The heat map creation unit 100B creates the heat map representing the emotion amount of each audience in association with the position of each audience in the venue of the event. In the event in which the seats are determined, the position of each audience can be specified by the seat position. The information on the seat position (information on the venue) is acquired in advance. The acquired information on the seat position is stored in, for example, the HDD 104.

Figure 6:
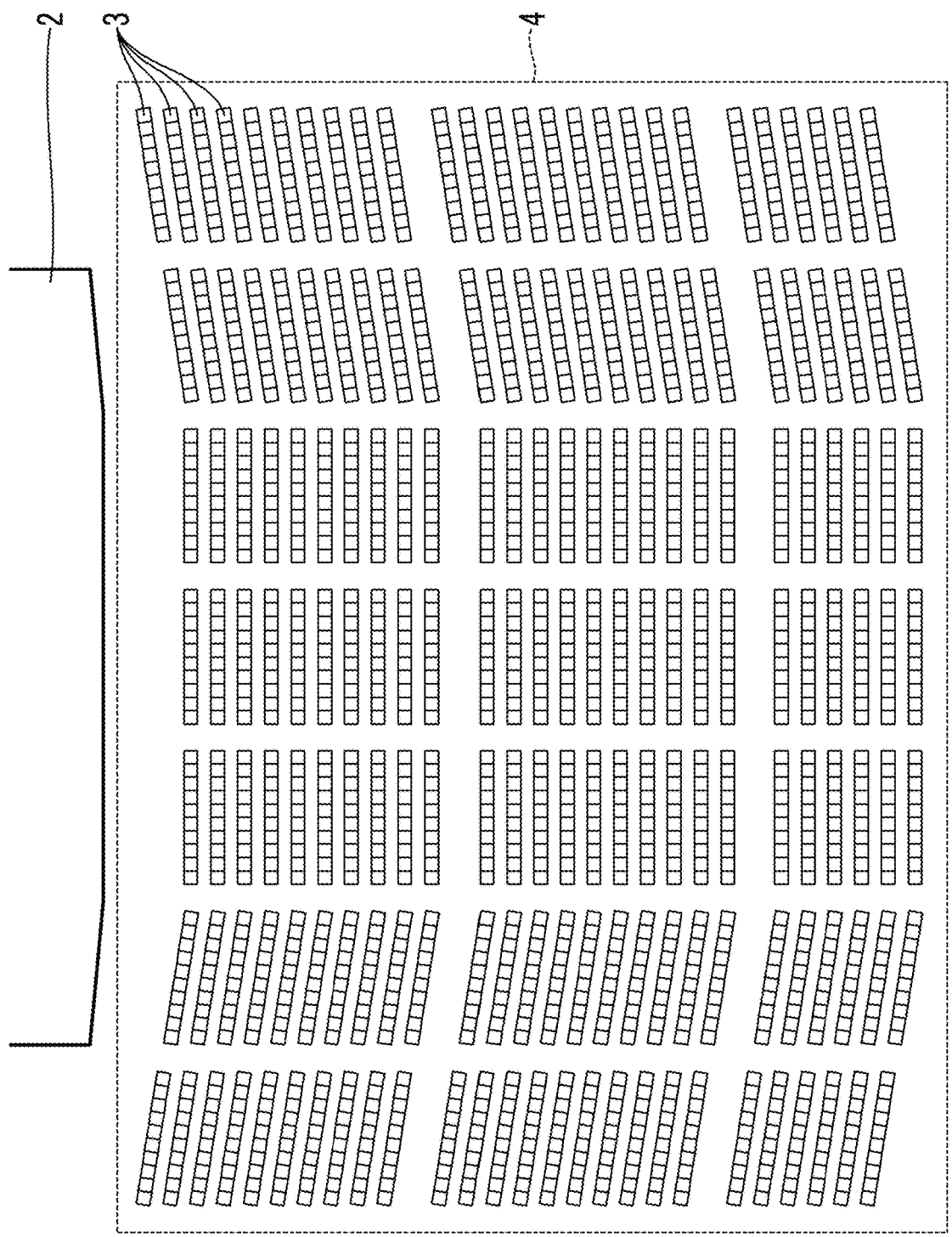
FIG. 6 is a plan view showing an example of an event venue.

FIG. 6 is a plan view showing an example of the event venue.

In FIG. 6, reference numeral 2 is a stage and reference numeral 3 is the seat. In addition, in FIG. 6, an area 4 shown by a broken line is an area for the audience seats, and is an area (first area) in which the audience is present. The imaging unit 20 images the area 4 and images each audience.

Figure 7:
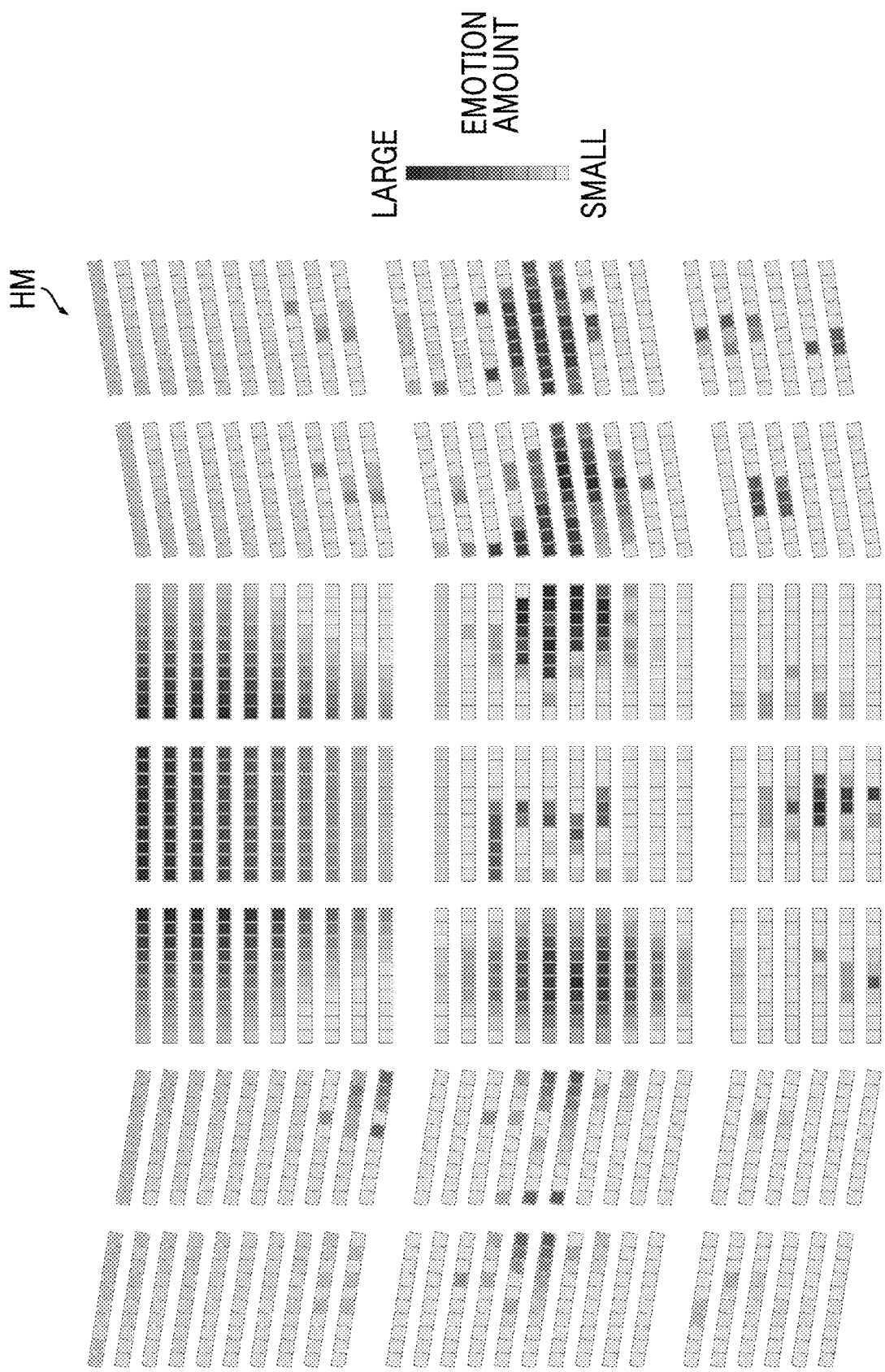
FIG. 7 is a diagram showing an example of a heat map created in the event venue shown in FIG. 6.

FIG. 7 is a diagram showing an example of the heat map created in the event venue shown in FIG. 6.

A heat map HM can be visualized by expressing a value of the emotion amount of the audience at each position by color or shading of color. In the example shown in FIG. 7, the position of each audience is specified by the position of the seat, and the value of the emotion amount is expressed by shading. It should be noted that the heat map does not necessarily have to be visualized. It is sufficient to be able to specify the position and the emotion amount of each audience.

The heat map is generated depending on a measurement interval of the emotion amount. That is, the heat map is created at the same interval as the measurement interval of the emotion amount. Since the emotion amount is measured continuously or intermittently along the time series, the heat map is also created continuously or intermittently along the time series. As a result, the heat map of the time series is generated. It should be noted that the creation interval of the heat map does not necessarily have to be the same as the measurement interval of the emotion amount, and may be created at different intervals.

The emotion transmission ability estimation unit 100C is an example of an estimation unit. The emotion transmission ability estimation unit 100C estimates the emotion transmission ability of each audience based on data of the heat map created by the heat map creation unit 100B. As described above, in the present embodiment, as the emotion transmission ability of the audience, the leadership (first ability), which is the ability to give emotion to surroundings, and the followership (second ability), which is the ability to accept emotion of surroundings are estimated. The leadership and the followership are estimated by the following method.

Figure 8:
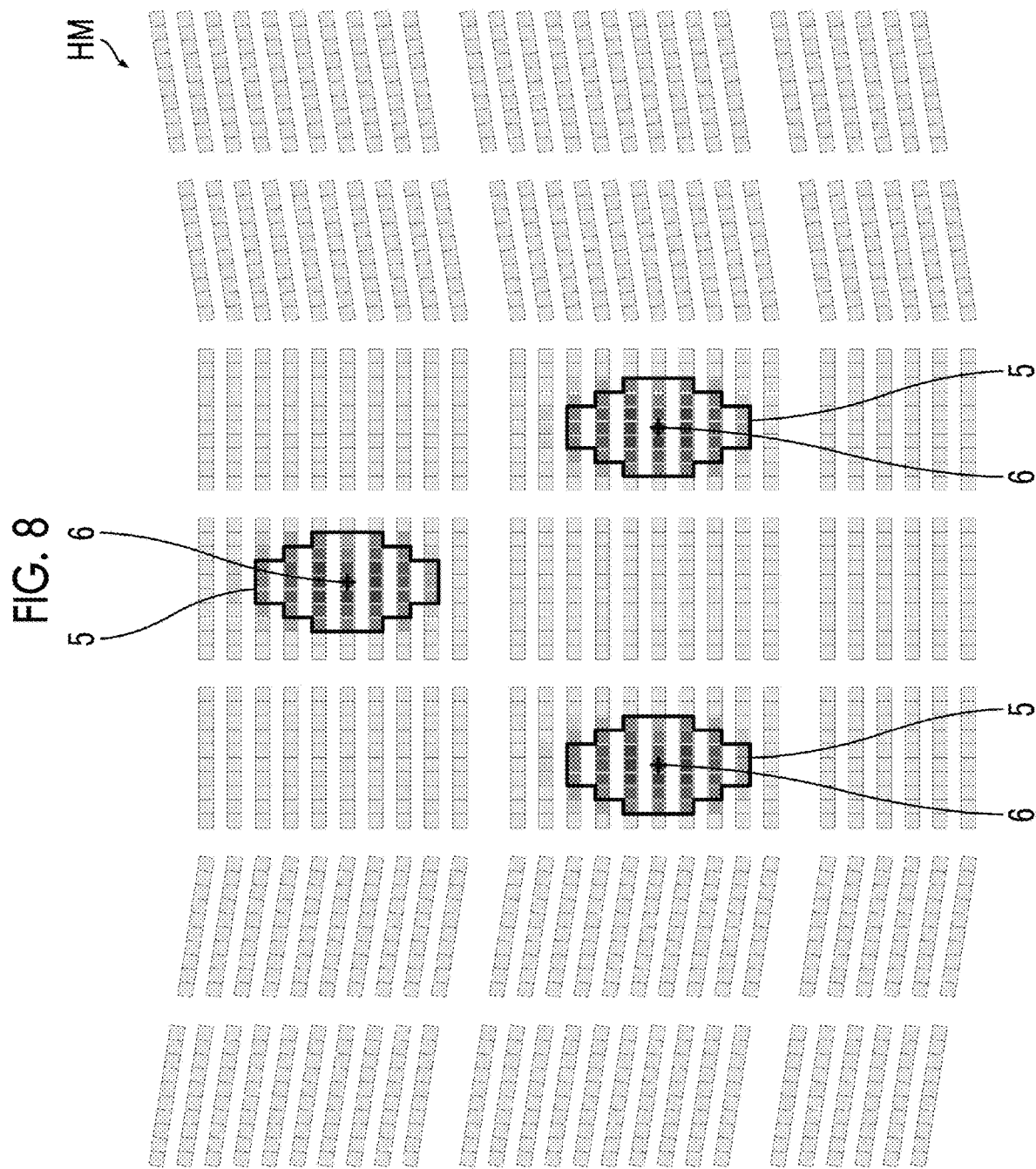
FIG. 8 is a diagram showing an example of an estimation method of the leadership.

FIG. 8 is a diagram showing an example of an estimation method of the leadership.

The emotion transmission ability estimation unit 100C extracts a region 5 in which the emotion amount is equal to or more than a threshold value from the heat map HM, obtains a centroid 6 of the extracted region 5, and estimates the leadership of each audience. That is, it is estimated that the audience who is present at the position of the centroid 6 is the audience who has the leadership. In this case, the other audiences are estimated to have no leadership.

In addition, the emotion transmission ability estimation unit 100C calculates the sum of the emotion amounts of the audience in the region 5, and models (quantifies) the leadership of the audience (audience at the position of the centroid 6) estimated to have the leadership.

In a case in which the leadership is estimated by this method, a size (area) of the region 5 to be extracted may be limited. That is, a configuration may be adopted in which a region having a certain size or more is extracted. In this method, a configuration can be adopted in which the leadership of each audience is estimated based on the heat map acquired at a specific timing. In addition, a configuration can be adopted in which the leadership of each audience is estimated based on the heat map of the time series acquired during a specific period (for example, the entire period of the event). In a case in which the leadership of each audience is estimated based on the heat map of the time series acquired for the specific period, for example, an integrated value of the leadership of each audience obtained from the image of each frame can be used as the leadership of the audience. In addition, an average value thereof can be used as the leadership of the audience.

Figure 9:
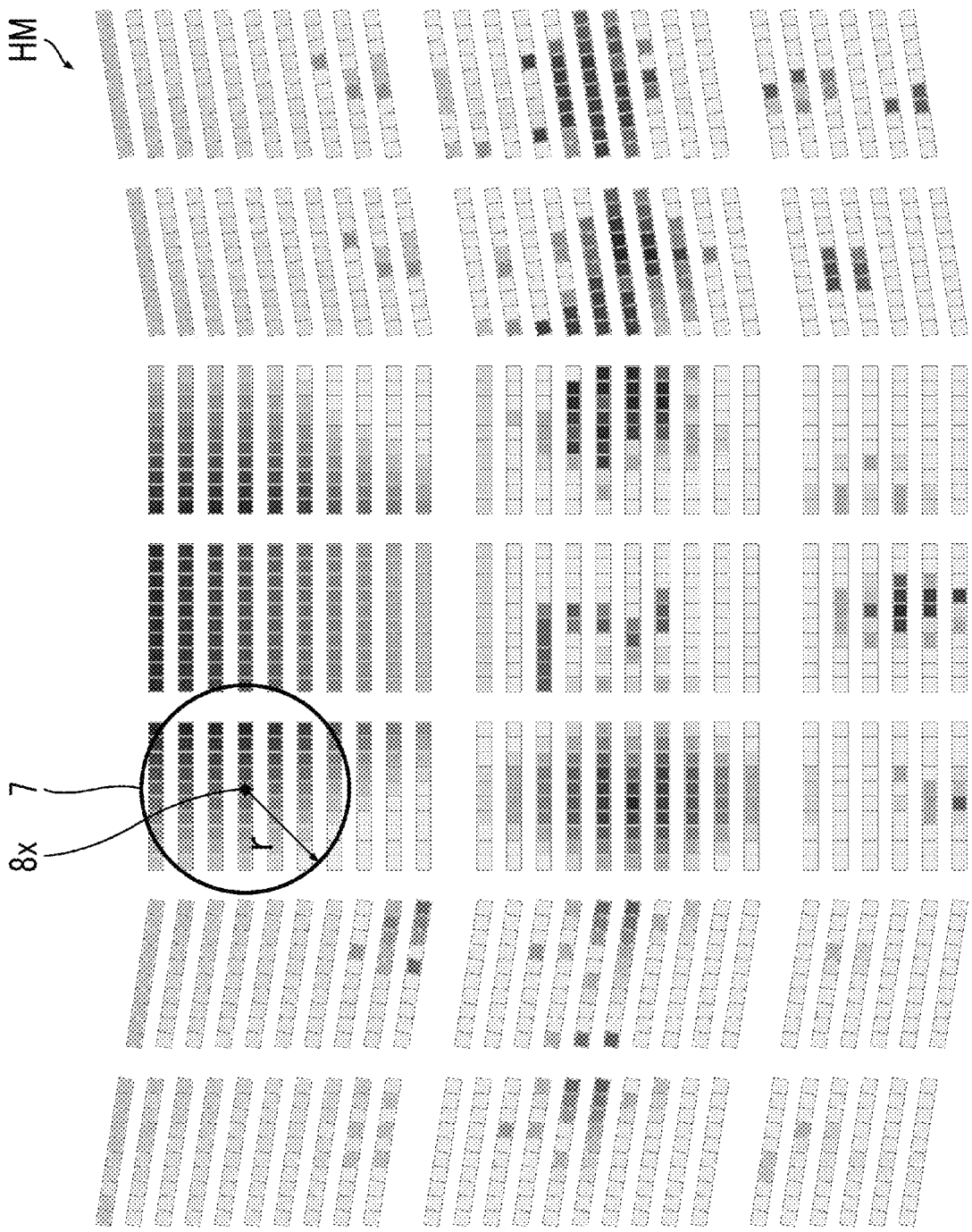
FIG. 9 is a diagram showing another example of the estimation method of the leadership.

FIG. 9 is a diagram showing another example of the estimation method of the leadership.

In this method, the leadership of each audience is individually estimated. The emotion transmission ability estimation unit 100C models (quantifies) the leadership of each audience by obtaining the sum of the emotion amounts of the audience positioned within a predetermined distance for each audience. Specifically, a circle having a radius r is set for each audience, and the sum of the emotion amounts of the audience (including audience positioned on the circle) positioned inside the circle is obtained for each audience, and the leadership of each audience is individually estimated. It should be noted that FIG. 9 shows an example in which the emotion amount of an audience $8x$ is obtained. In this case, as shown in FIG. 9, a circle 7 having the radius r centered on the audience $8x$ is set. The sum of the emotion amounts of the audience positioned inside the set circle 7 is calculated to obtain the emotion amount of the audience $8x$. By performing the same arithmetic processing for each audience, the emotion amount of each audience can be individually obtained. According to this method, the leadership of each audience can be individually grasped. It is preferable to appropriately set the radius r of the circle indicating a range of the predetermined distance depending on the content of the event, the size of the venue, and the like. It should be noted that, in this method, a configuration can be adopted in which the leadership of each audience is estimated based on the heat map acquired at a specific timing. In addition, a configuration can be adopted in which the leadership of each audience is estimated based on the heat map of the time series acquired during a specific period (for example, the entire period of the event). In a case in which the leadership of each audience is estimated based on the heat map of the time series acquired for the specific period, for example, an integrated value of the leadership of each audience obtained from the image of each frame can be used as the leadership of the audience. In addition, an average value thereof can be used as the leadership of the audience.

Figure 10:
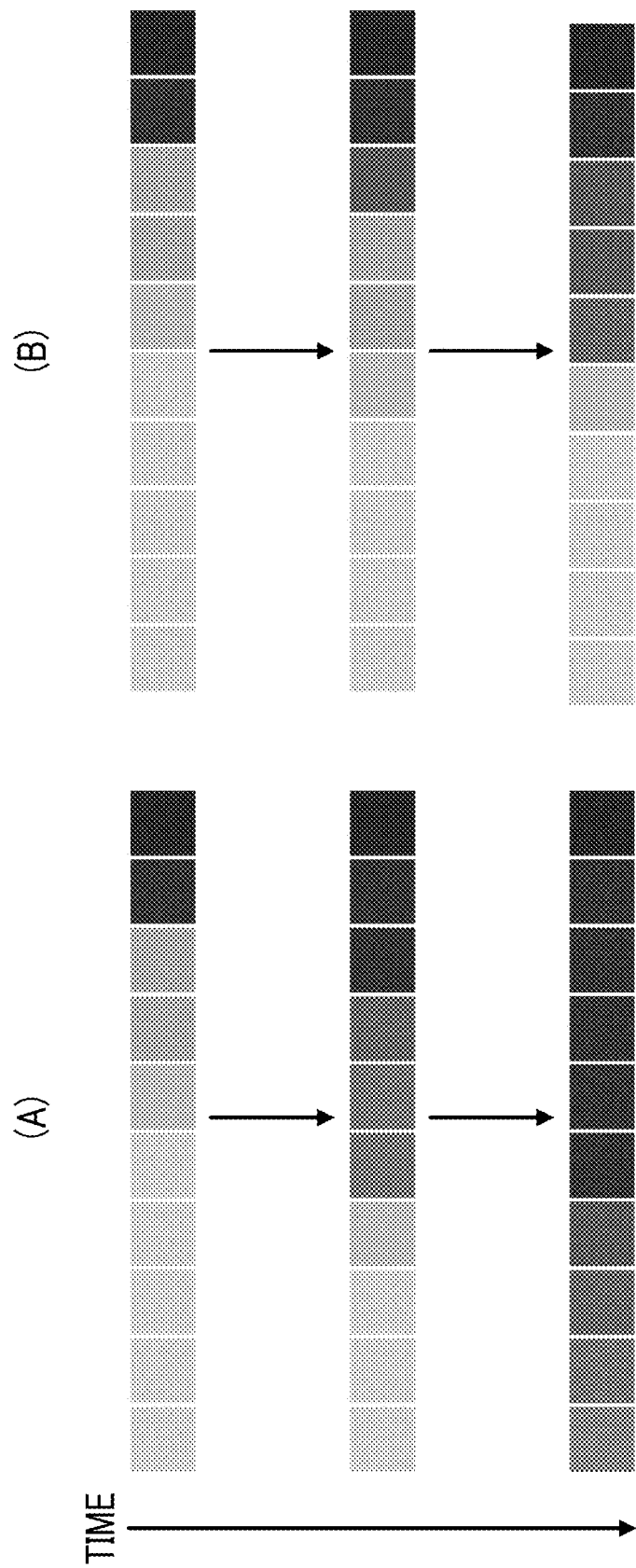
FIG. 10 is a diagram showing a temporal change in an emotion amount of each audience in a certain seat row.

The followership is estimated by using the heat map of the time series. FIG. 10 is a diagram showing a temporal change in the emotion amount of each audience in a certain seat row. (A) of FIG. 10 shows the temporal change in the emotion amount of the seat row of the audience having high followership, and (B) of FIG. 10 shows the temporal change in the emotion amount of the seat row of the audience having low followership. As shown in FIG. 10, the seat row of the audience having the high followership has a high propagation rate of the emotion amount. On the other hand, in the seat row of the audience having low followership, the propagation rate of the emotion amount is slow. In this way, the followership of each audience can be estimated from the propagation rate of the emotion amount. The emotion transmission ability estimation unit 100C obtains the propagation rate of the emotion amount from the heat map of the time series (heat map created at the predetermined time intervals), and models (quantifies) the followership of each audience.

The emotion transmission ability information output unit 100D outputs (transmits) the information on the emotion transmission ability of each audience estimated by the emotion transmission ability estimation unit 100C, that is, the information on the leadership and the information on the followership of each audience to the database device 200. The emotion transmission ability estimation unit 100C outputs (transmits) the information on the leadership and the followership of each audience to the database device 200 via the communication unit 107. In this case, the emotion transmission ability information output unit 100D outputs the information on the leadership and the followership of each audience in association with the information on the position of the audience. The information on the position of the audience is specified by the seat position.

As described above, the emotion transmission ability estimation device 100 generates the heat map from the information on the emotion amount of each audience, and estimates the emotion transmission ability (leadership and followership) possessed by each audience from the generated heat map. It should be noted that emotion amounts of all the audiences are not always measured at each timing (frame), the heat map is generated based on the information on the audience whose emotion amount is measured. For the audience whose emotion amount is not measured, the heat map is generated by replacing the emotion amount with a predetermined value.

Database Device

The database device 200 generates a database of a customer (audience) based on the information on the emotion transmission ability (leadership and followership) of each audience estimated by the emotion transmission ability estimation device 100.

The database device 200 is configured by a computer comprising a CPU, a ROM, a RAM, an HDD, an operation unit (for example, a keyboard, a mouse, or a touch panel), a display unit (for example, a liquid crystal display), a communication unit, and the like (see FIG. 4). The database device 200 is communicably connected to the emotion transmission ability estimation device 100, the placement decision device 300, and the like via the communication unit. A connection form thereof may be wired or wireless.

Figure 11:
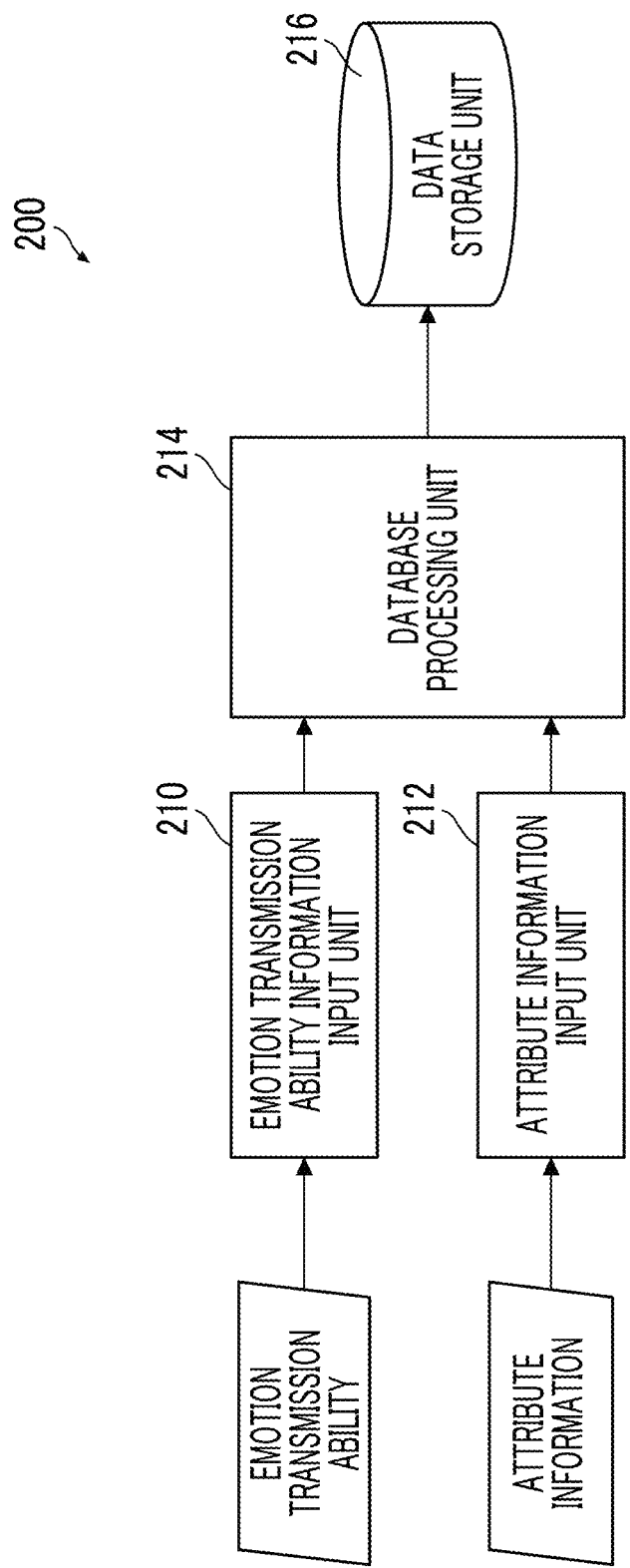
FIG. 11 is a block diagram of a function of the emotion transmission ability estimation device.

FIG. 11 is a block diagram of a function of the emotion transmission ability estimation device.

As shown in FIG. 11, the database device 200 has the functions of an emotion transmission ability information input unit 210, an attribute information input unit 212, a database processing unit 214, and a data storage unit 216.

The emotion transmission ability information input unit 210 receives the input of the information on the emotion transmission ability of each audience output (transmitted) from the emotion transmission ability estimation device 100. The information on the emotion transmission ability is input to (received by) the emotion transmission ability information input unit 210 via the communication unit. The information on the emotion transmission ability of each audience is input in association with information on the position (seat position) of each audience.

The database processing unit 214 generates a customer database based on the input information on the emotion transmission ability (leadership and followership) of each audience. That is, the database (customer database) is generated in which the audience and the information on the emotion transmission ability of the audience are recorded in association with each other. The data storage unit 216 stores the customer database.

FIG. 12 is a diagram showing an example of the customer database.

A user identification (ID) is assigned to each customer. The user ID is an identification code for specifying an individual. The information on the emotion transmission ability (leadership and followership) of each audience who is the customer is stored in association with the user ID of each customer.

It should be noted that the information on the user ID of the audience at each seat position is input and held in the database device 200 in advance. For example, the information on the user ID is acquired from an external device via the communication unit and stored in the HDD. The database processing unit 214 specifies the user ID from the seat position with reference to this information, and acquires the emotion transmission ability (leadership and followership) of the audience associated with the seat position.

Attribute information of the customer is stored in the customer database in association with each other. Examples of the attribute information include information, such as the age, the gender, the number of repeats, the purchasing information, and the preference of the customer (audience).

Examples of the number of repeats include the number of times of participation in the same event (for example, the number of times of participation in the concert of the same artist, and the number of times of watching the match of the same team). Examples of the purchasing information include information on a purchase history of tickets, goods, and the like sold by an event organizer. Examples of the preference include information on the preference of the event, and is collected by, for example, a questionnaire to the customer. Alternatively, the preference is estimated based on the purchasing information. The attribute information is acquired via the attribute information input unit 212. The attribute information input unit 212 communicates with an external device (for example, a ticketing terminal) via the communication unit, and receives the input of the attribute information. The attribute information is input in association with the user ID.

The functions of the emotion transmission ability information input unit 210, the attribute information input unit 212, and the database processing unit 214 are realized by executing a predetermined program by the CPU. This program is stored, for example, in the HDD. The data storage unit 216 is configured by, for example, the HDD. The data storage unit 216 is an example of a storage unit. The attribute information input unit 212 is an example of an attribute information reception unit.

As described above, the database device 200 generates the database (customer database) of the information on the emotion transmission ability of each customer and the attribute information. The database is added or updated each time the event is held. That is, the database is added or updated each time new information (information on the emotion transmission ability and the attribute information) is acquired. As a result, it is possible to collect information on a large number of customers and information on the emotion transmission ability at a large number of events.

Placement Decision Device

The placement decision device 300 decides the placement of the audience in a case in which a new event is held. The placement decision device 300 decides the placement of the audience by using the information in the customer database stored in the database device 200.

The placement decision device 300 is configured by a computer comprising a CPU, a ROM, a RAM, an HDD, an operation unit (for example, a keyboard, a mouse, or a touch panel), a display unit (for example, a liquid crystal display), a communication unit, and the like (see FIG. 4). The placement decision device 300 is communicably connected to the emotion transmission ability estimation device 100, the database device 200, and the like via the communication unit. A connection form thereof may be wired or wireless.

Figure 13:
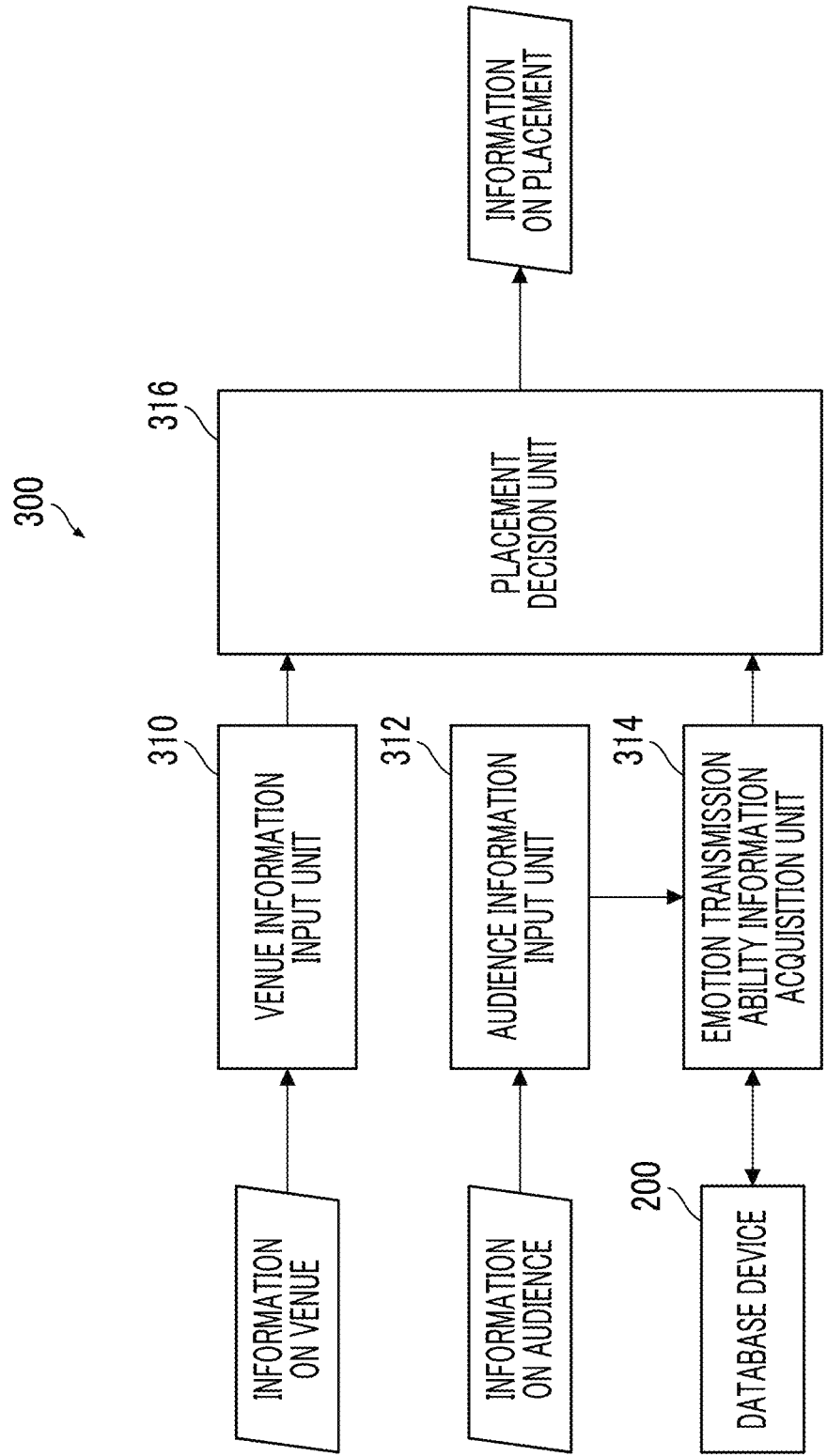
FIG. 13 is a block diagram of a function of a placement decision device.

FIG. 13 is a block diagram of a function of the placement decision device.

As shown in FIG. 13, the placement decision device 300 has the functions of a venue information input unit 310, an audience information input unit 312, an emotion transmission ability information acquisition unit 314, and a placement decision unit 316. The function of each unit is realized by executing a predetermined program by the CPU. This program is stored, for example, in the HDD.

The venue information input unit 310 receives the input of the information on the venue in which the event is held. The information on the venue is the information on the area (second area) in which the audiences are placed. More specifically, the information on the venue is information on the placement of the audience seat in the area (information on the placement position of the seat). The information on the venue is input to (received by) the venue information input unit 310 via the communication unit.

It should be noted that the information on the venue can be stored in the HDD or the like in advance. In this case, the information on the venue is acquired by reading the information out the HDD or the like.

The audience information input unit 312 receives the input of the information on the audience who participates in the event (viewing the event, watching the sports, and the like). This information is the information on a plurality of the persons placed in the second area. The information on the audience is the information for specifying individual audience. In the present embodiment, the information on the user ID is input. The information on the audience is input to (received by) the audience information input unit 312 via the communication unit. For example, the information on the audience is transmitted from the ticketing terminal or the like, and is input to (received by) the audience information input unit 312 via the communication unit. The audience information input unit 312 is an example of a person information reception unit.

The emotion transmission ability information acquisition unit 314 accesses the database device 200 and acquires the information on the emotion transmission ability (leadership and followership) of each audience who participates in the event. The emotion transmission ability information acquisition unit 314 is an example of an information acquisition unit.

It should be noted that the information on the emotion transmission ability of all the audiences is not always registered in the customer database. Therefore, the emotion transmission ability information acquisition unit 314 acquires the information on the emotion transmission ability only for the audience registered in the customer database.

The placement decision unit 316 decides the placement (seat placement) of each audience in the event venue based on the information on the emotion transmission ability (leadership and followership) of each audience acquired by the emotion transmission ability information acquisition unit 314. Specifically, based on the information on the emotion transmission ability of each audience, the change of the emotion amount of each audience is simulated, and the placement that maximizes the emotion amount evenly in the venue is obtained. In this case, the information on the emotion transmission ability obtained at the same type of event is used as the information on the emotion transmission ability to be used. That is, the information on the emotion transmission ability of emotion corresponding to the content of the event to be held is used. For example, in the concert, the information on the emotion transmission ability corresponding to emotion of joy and pleasure (information on the emotion transmission ability based on the emotion amount calculated from the levels of emotion of joy and pleasure) is used. In addition, in the case of watching the sports, the information on the emotion transmission ability corresponding to the amplitude of emotion (information on the emotion transmission ability based on the emotion amount calculated from the magnitude of the amplitude of emotion) is used.

It is possible to adopt a so-called thermal simulation method for the simulation. That is, the change of the emotion amount is simulated by using a known heat simulation (heat analysis) method by regarding the "leadership" as a "calorific value", the "followership" as a "thermal conductivity", and the "emotion amount" as a "heat amount".

Figure 14:
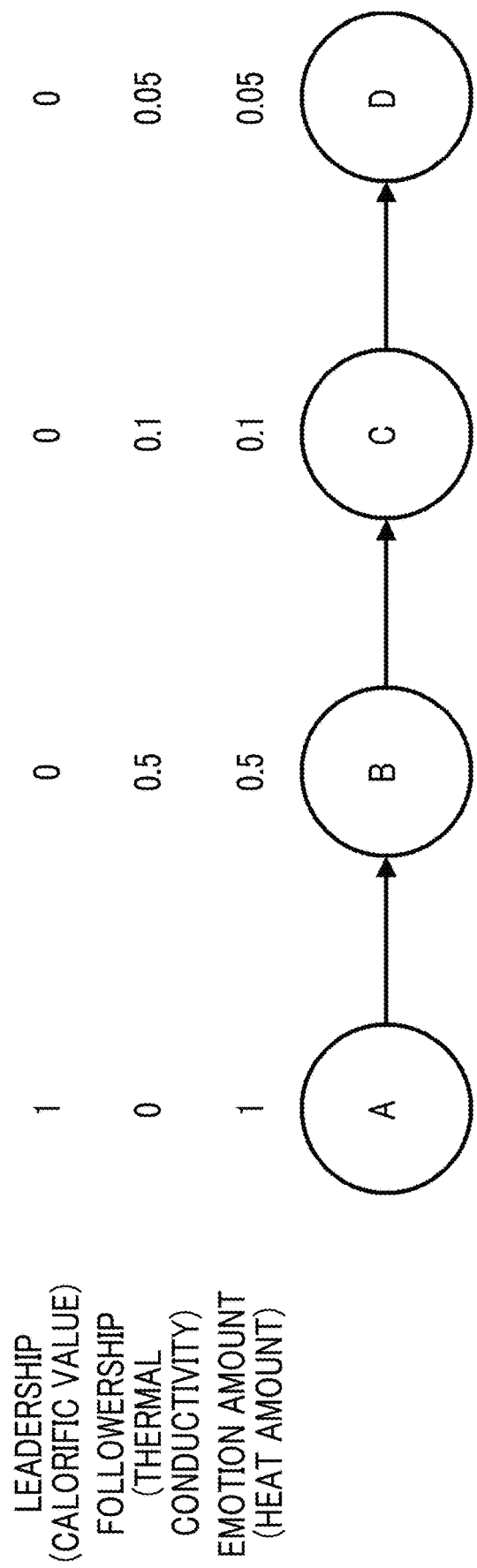
FIG. 14 is a conceptual diagram of a simulation of the emotion amount.

FIG. 14 is a conceptual diagram of the simulation of the emotion amount.

FIG. 14 shows an image in which the emotion amount of an audience A, who has the leadership, is transmitted to an audience B, an audience C, and an audience D in a case in which the audience A, the audience B, the audience C, and the audience D are arranged in a row. An aspect is simulated in which the emotion amount (heat amount) propagates by using the "calorific value" as the "leadership" and the "thermal conductivity" as the "followership" as the parameters of the simulation. This simulation is performed to obtain the placement in which the emotion amount is uniform and maximized.

It should be noted that the information on the emotion transmission ability is not always acquired for all the audiences. For the audiences whose information on the emotion transmission ability is not acquired, the simulation is performed by replacing the information on the emotion transmission ability with a predetermined value.

The information on the placement of the audience decided by the placement decision unit 316 is stored in the HDD. In addition, the information on the placement is displayed on the display unit as needed.

As described above, the placement decision device 300 uses the information in the customer database (information on the emotion transmission ability of each audience) to decide the placement of the audience in a case in which a new event is held. The device configured by the placement decision device 300 and the database device 200 configures an information processing apparatus that decides the placement of the audience in a case in which a new event is held.

Action

The processing performed by the information processing system 1 according to the present embodiment is roughly classified into (1) processing of obtaining the emotion transmission ability of the audience and creating the database thereof (customer database), and (2) processing of deciding the placement of the audience by using the created database. In the following, each processing will be described separately.

Figure 15:
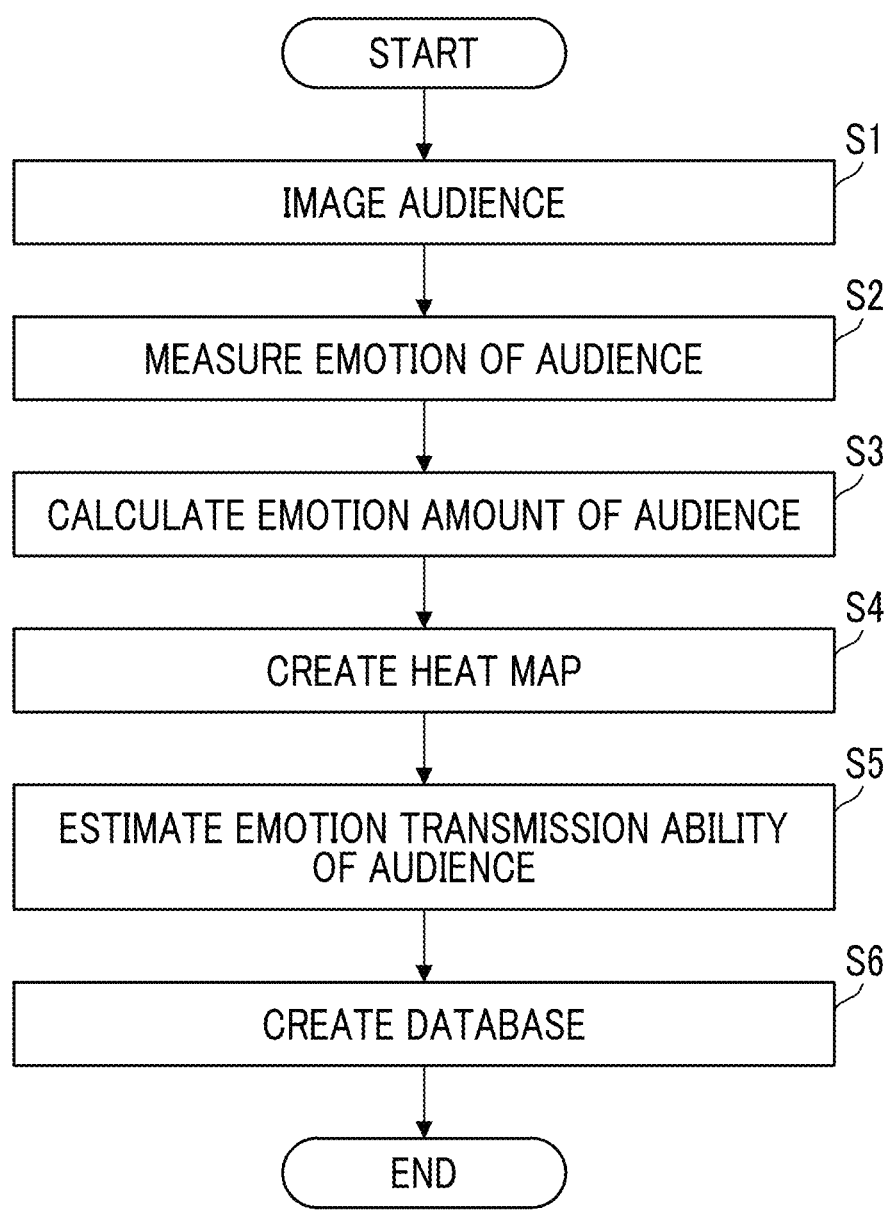
FIG. 15 is a flowchart showing a processing procedure (information processing method) until a database is created.

(1) Processing of Obtaining Emotion Transmission Ability of Audience and Creating Customer Database FIG. 15 is a flowchart showing a processing procedure (information processing method) until the database is created.

First, the audience is imaged in the event venue (step S1). That is, in the area (first area) of the audience seats, the audience 8 who views the event, watches the sports, or the like is imaged.

Then, emotion of each audience is measured based on the image obtained by imaging (step S2). That is, the face of each audience is detected from the image obtained by imaging, and emotion of each audience is measured based on the image of the detected face. More specifically, emotion is measured (estimated) based on the facial expression.

Then, the emotion amount of each audience is calculated based on the measured emotion (step S3). The emotion amount is calculated by selecting a calculation target depending on the content of the event. For example, in the concert, the levels of emotion of joy and pleasure are calculated as the emotion amount. In watching the sports, the magnitude of amplitude of the emotion is calculated as the emotion amount. In the steps up to this point, the emotion amount of each audience is measured.

Then, based on the measured information on each emotion amount, the heat map is created in which the emotion amount of each audience is associated with the position of each audience (step S4). The position of each audience is specified by the seat position of each audience. Therefore, the heat map of the emotion amount for each seat (audience seat) is created (see FIG. 7).

Then, the emotion transmission ability of each audience is estimated based on the created heat map (step S5). In the system according to the present embodiment, a degree of the leadership and a degree of the followership are estimated as the emotion transmission ability possessed by each audience. In the steps up to this point, the emotion transmission ability of each audience is obtained.

Then, the customer database is created from the estimated information on the emotion transmission ability of each audience (step S6). That is, the database in which the information on the emotion transmission ability is recorded is created for each audience. Each audience is specified by the seat position thereof. The attribute information of each audience is also recorded in the customer database in association with each other.

The database of the emotion transmission ability is created by a series of the steps described above.

(2) Processing of Deciding Placement of Audience by Using Database

Figure 16:
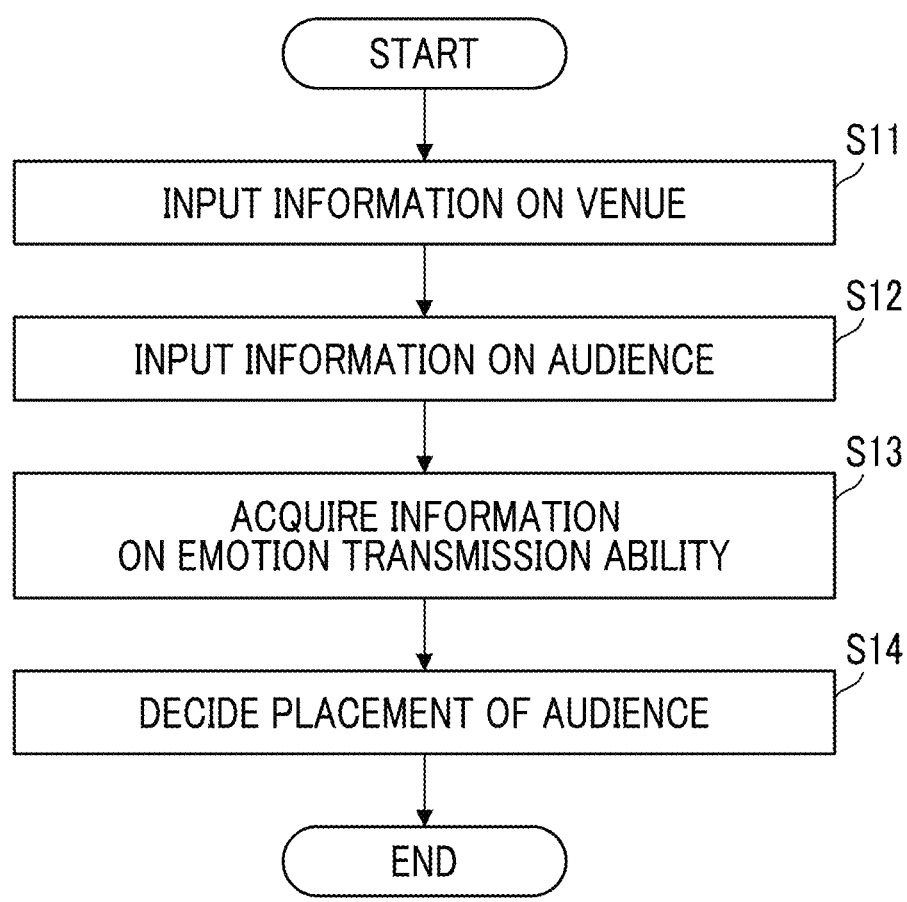
FIG. 16 is a flowchart showing a procedure (information processing method) of audience placement decision processing using the customer database.

FIG. 16 is a flowchart showing a procedure (information processing method) of audience placement decision processing using the customer database.

First, the information on the venue is input (step S11). That is, the information on the venue in which the event is held is input. This information is the information on the area (second area) in which the audience is placed in the event venue. Specifically, this information is the information on the placement of the seat in the event venue.

Then, the information on the audience is input (step S12). That is, the information on the audience who participates in the event is input. This information is the information on the audience placed in the audience seat, and is the information for specifying an individual in the customer database.

Then, the information on the emotion transmission ability of each audience (information on the audience placed in the audience seat in the event venue) is acquired from the customer database (step S13). It should be noted that the information on the emotion transmission ability can be acquired for only the audience whose information is registered in the customer database.

Then, the placement of each audience is decided based on the acquired information on the emotion transmission ability of each audience (step S14). Specifically, the information on the emotion transmission ability of each audience is used to simulate the change of the emotion amount, and the placement in which the emotion amount is uniform and maximized throughout the venue is obtained. For the audience (new customer) whose information on their emotion transmission ability is not present, the simulation is performed by replacing the information on their emotion transmission ability with the predetermined value.

The placement of the audience is decided by a series of the steps described above.

With the information processing system according to the present embodiment, the emotion transmission ability of each audience is grasped, and the audience is placed by using the information, so that the placement that can maximize the satisfaction of the audiences is possible.

Second Embodiment

In a case in which the placement of the audience is decided, it is not possible to acquire the information on the emotion transmission ability for the audience (new customer) who is not registered in the customer database. In addition, even in a case in which the audience is registered in the customer database, the information on the emotion transmission ability to be controlled may not be registered. For example, in a case in which the event, such as watching the sports, is held, the above case corresponds to a case in which only the information on the emotion transmission ability measured at the concert is registered, a case in which only the information on the emotion transmission ability measured at the concert with completely different contents is registered, and the like.

With the information processing system according to the present embodiment, in a case in which the placement of the audience is decided, the emotion transmission ability of the audience (of which information is not present in the customer database (including a case in which the corresponding information on the emotion transmission ability is not present) is discriminated from the information possessed by the audience and used for the information in a case in which the audience is placed.

With the information processing system according to the present embodiment, the placement decision device 300 has a function of discriminating the emotion transmission ability of the audience (customer).

Figure 17:
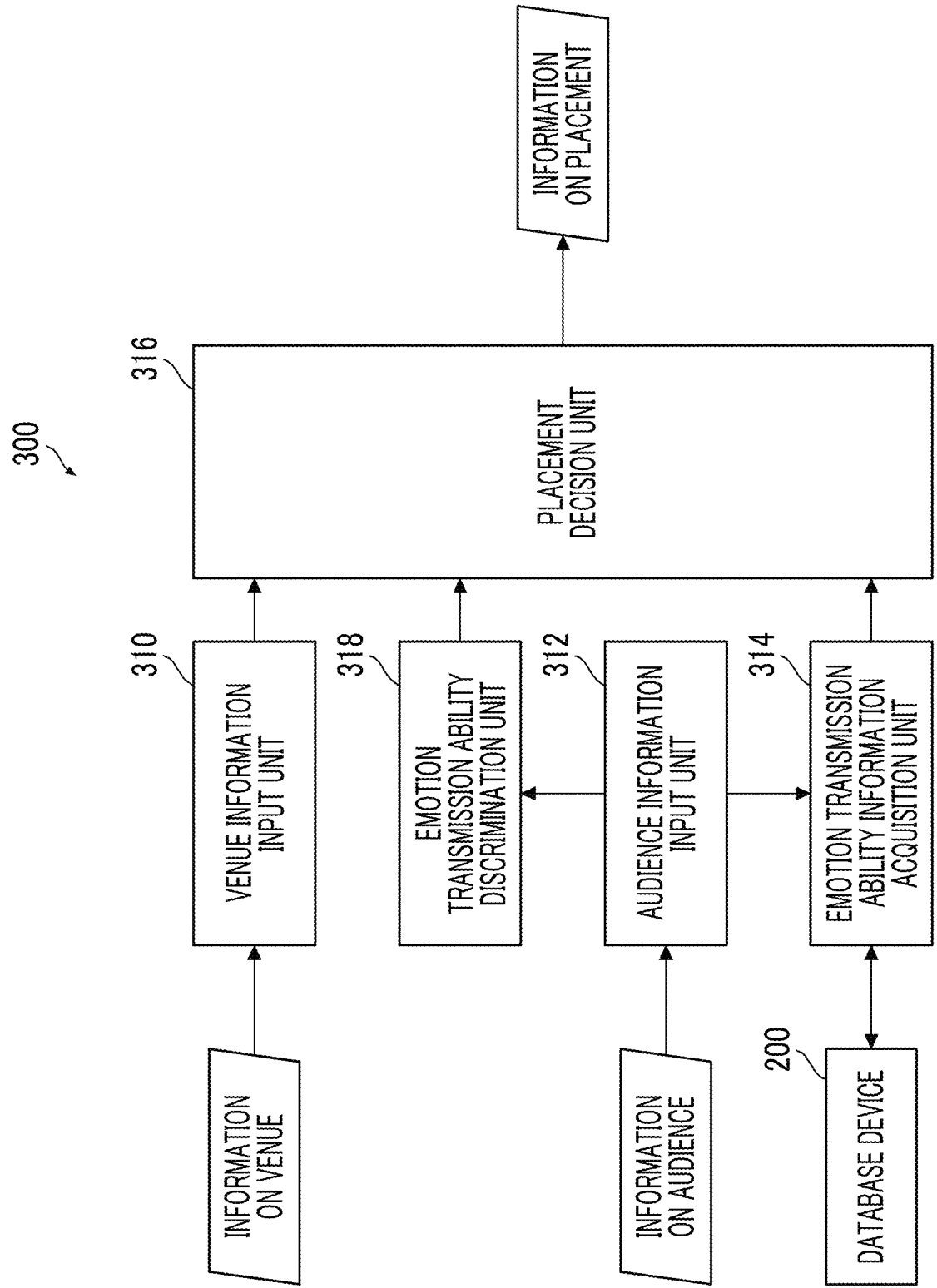
FIG. 17 is a block diagram of a function of a placement decision device according to a second embodiment.

FIG. 17 is a block diagram of a function of the placement decision device according to the present embodiment.

As shown in FIG. 17, the placement decision device 300 according to the present embodiment is different from the placement decision device 300 according to the first embodiment in that a function of an emotion transmission ability discrimination unit 318 is further provided. In the following, only the difference will be described.

The emotion transmission ability discrimination unit 318 discriminates the emotion transmission ability of the audience whose information is not present in the customer database (including a case in which the corresponding information on the emotion transmission ability is not present). The emotion transmission ability discrimination unit 318 is an example of a discrimination unit. The emotion transmission ability discrimination unit 318 discriminates (estimates) the emotion transmission ability of the audience based on the attribute information of the audience (for example, the information, such as the age, the gender, the number of repeats, the purchasing information, and the preference). In the present embodiment, the emotion transmission ability discrimination unit 318 discriminates (estimates) the emotion transmission ability of the audience by using a discrimination model generated by machine learning. This discrimination model can be generated by, for example, machine learning (for example, deep learning) by using the information registered in the customer database.

As described above, with the information processing system according to the present embodiment, even for the audience whose information is not present in the database, it is possible to obtain an approximate value of the emotion transmission ability. As a result, it is possible to obtain a more appropriate placement of the audience.

Third Embodiment

As described above, the placement of the audience is decided to be the placement in which the emotion amount is uniform and maximized throughout the venue. However, the decided placement may not reach the desired quality. For example, in a situation in which there is a shortage of the audience to be the leader (audience having the high leadership), it is difficult to place the audience at a desired quality level. With the information processing system according to the present embodiment, in a case in which the placement of the audience is decided, the placement of the audience is decided by adding the person having the emotion transmission ability (particularly the person having the high leadership) as needed.

Figure 18:
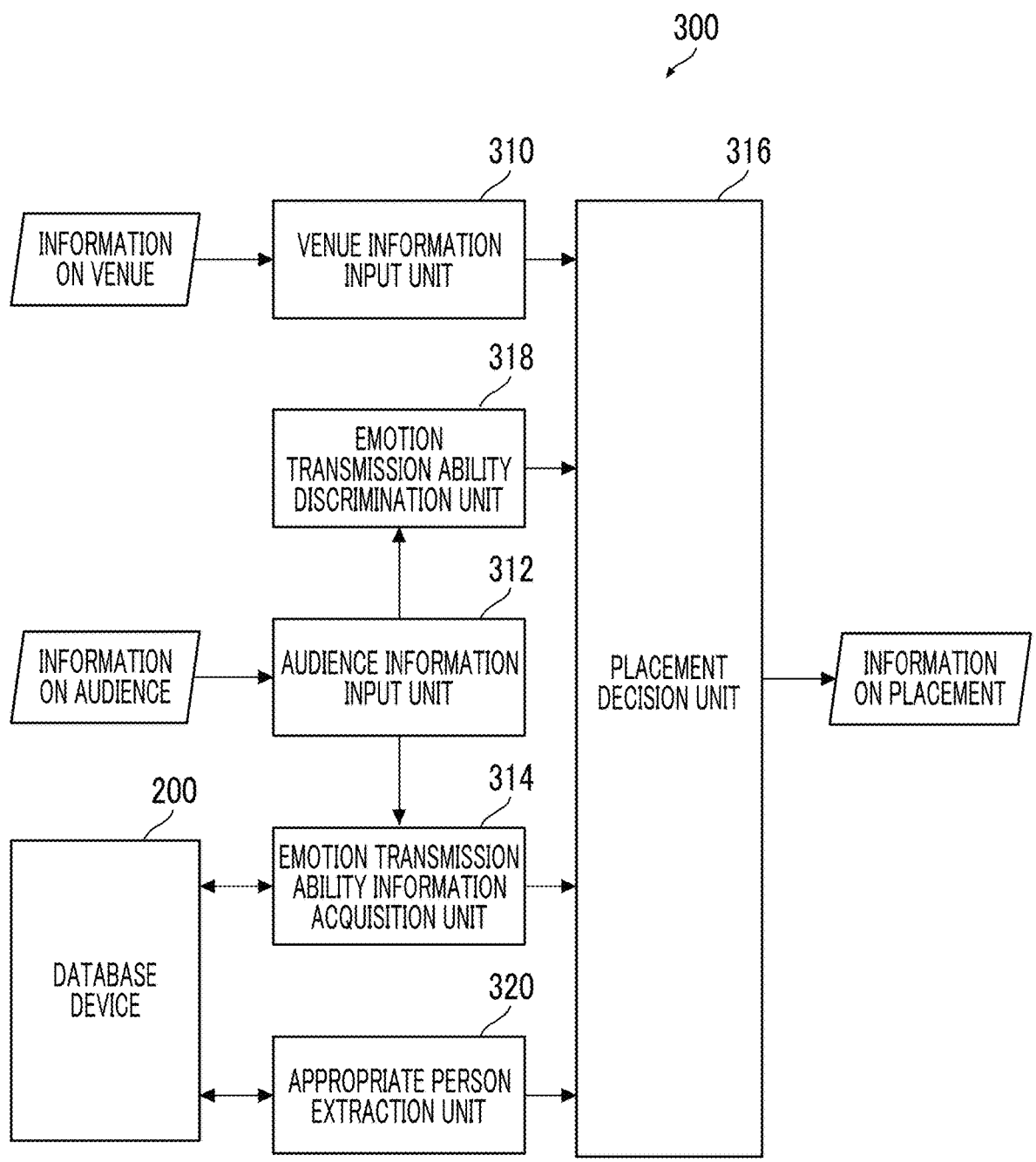
FIG. 18 is a block diagram of a function of a placement decision device according to a third embodiment.

FIG. 18 is a block diagram of a function of the placement decision device according to the present embodiment.

As shown in FIG. 18, the placement decision device 300 according to the present embodiment is different from the placement decision devices 300 according to the first and second embodiments in that a function of an appropriate person extraction unit 320 is further provided. In the following, only the difference will be described.

The appropriate person extraction unit 320 extracts the person (customer) having the high emotion transmission ability from among the customers registered in the customer database, and acquires the information on the emotion transmission ability thereof. The appropriate person extraction unit 320 is an example of an extraction unit. In the present embodiment, the person having the high leadership is extracted and the information on the emotion transmission ability thereof is acquired. It should be noted that in a case of extraction, the person having the high emotion transmission ability of emotion corresponding to the content of the event to be held is extracted.

The extraction processing is performed in response to an instruction from an operator. The operator designates the number of persons to be extracted and the type of emotion, and gives an instruction for executing the extraction processing.

In a case in which the appropriate person extraction unit 320 performs the extraction processing of the person having the high emotion transmission ability, the placement decision unit 316 adds the person and performs the placement decision processing.

The operator appropriately increases or decreases the number of persons to be extracted and executes placement decision processing. As a result, the placement at the desired quality level can be realized.

The information on the extracted person is presented to the operator (for example, displayed on the display unit). The operator performs inviting to the event, gives special treatment, and the like.

As described above, with the information processing system according to the present embodiment, since the placement of the audience is adjusted by appropriately adding the person having the high emotion transmission ability, the quality can be kept to be equal to or more than a certain level.

Fourth Embodiment

The information processing system according to the present embodiment receives a request for the placement from the audience who participates in the event and decides the placement of each audience.

Figure 19:
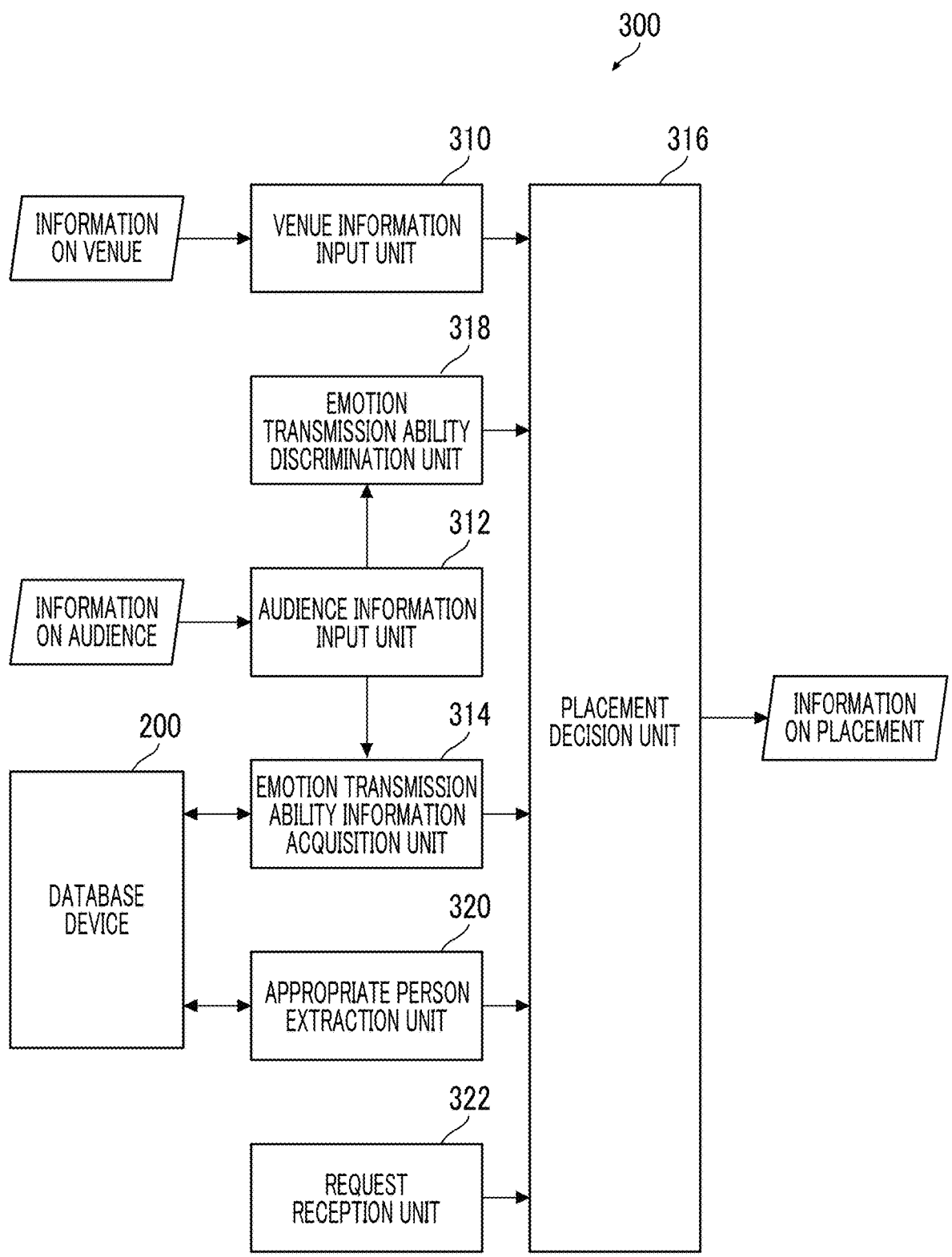
FIG. 19 is a block diagram of a function of a placement decision device according to a fourth embodiment.

FIG. 19 is a block diagram of a function of the placement decision device according to the present embodiment.

As shown in FIG. 19, the placement decision device 300 according to the present embodiment is different from the placement decision devices 300 according to the first to third embodiments in that a function of a request reception unit 322 is further provided. In the following, only the difference will be described.

The request reception unit 322 performs processing of receiving the request for the placement from the audience who participates in the event. Specifically, the request reception unit 322 receives the request for whether or not to emphasize the atmosphere of the place, and whether or not to want to be influenced by surroundings. The placement decision unit 316 decides the placement of each audience in consideration of the received request. For example, the placement decision unit 316 places the customer who emphasizes the atmosphere of the place and wants to be influenced by surroundings near the person having the high leadership. Conversely, the placement decision unit 316 places the customer who does not want to be influenced by surroundings away from the person having the high leadership.

In this way, by receiving the request for the placement from the audience and deciding the placement, the placement with more satisfaction can be realized.

It should be noted that a configuration can be adopted in which the requests of all the audiences are received, but in a case in which the requests of all the audiences are received, the placement at the desired quality level may not be realized. In such a case, a configuration can be adopted in which the request is received only for a certain audience. For example, a configuration can be adopted in which the request is received for only the customer with a high total payment amount.

A configuration can be adopted in which the request for the placement is received at the time of application, and the information can be recorded as the attribute information of the audience.

Modification Example

Modification Example of Emotion Amount Measurement Device

In the embodiments described above, the configuration has been adopted in which the emotion amount is measured as the index of emotion and the level of the specific emotion or the amplitude of emotion is calculated, but a method of calculating the emotion amount is not limited to this. It is sufficient to be able to obtain emotion numerically. Therefore, for example, a configuration can be adopted in which both the level of specific emotion and the amplitude of emotion are calculated to calculate the emotion amount (index of emotion).

In addition, in the embodiments described above, the configuration has been adopted in which the emotion is measured based on the expression of the audience (expression recognized from the image) and the emotion amount is calculated, but the emotion amount can be calculated by using other information.

For example, in a case in which biological information of the audience (heart rate, pulse, body temperature, and the like) can be collected, the emotion amount can be calculated by using this information. In this case, the measurement device body has a function of a biological information reception unit that receives the biological information of the audience. The biological information of the audience is measured by using sensors (heart rate monitor, thermometer, and the like) attached to each audience.

In addition, for example, in a case in which voice information (voice volume, voice quality, and the like) uttered by the audience can be collected, the emotion amount can be calculated by using this information (at least one of the voice volume or the voice quality). In this case, the measurement device body has a function of a voice information reception unit that receives voice information uttered by the audience. The information on voice uttered by the audience is collected, for example, by installing a microphone in the seat (audience seat). Alternatively, the information on voice uttered by the audience is collected by attaching a microphone to the audience. The information on voice does not necessarily have to be individual voice, but can also be collected as regional voice. In this case, voice collected in the region is voice of each audience belonging to the region.

In addition, for example, in a case in which information on vibration of the audience can be collected, the emotion amount can be calculated by using this information. In this case, the measurement device body comprises a vibration information reception unit that receives the information on vibration of the audience. The information on vibration of the audience is collected, for example, by installing a sensor that measures vibration in the seat (audience seat). The information on vibration does not necessarily have to be individual voice, but can also be collected as regional voice. In this case, vibration collected in the region is vibration of each audience belonging to the region.

It is possible to calculate the emotion amount by appropriately combining these pieces of information. In addition, in a case in which emotion of the audience is measured based on the captured image, a configuration can be adopted in which emotion of the audience is measured based on the image of the audience captured from a plurality of directions. In this case, the same area is imaged from a plurality of directions to acquire the image for measurement.

The emotion amount may be measured in real time or after the event is finished. In a case in which the emotion amount is measured after the event is finished, the image of the audience is captured during the event, and the image data is recorded.

In addition, the emotion amount does not necessarily have to be measured throughout the entire duration of the event. The emotion amount can also be measured at predetermined time intervals. In addition, the emotion amount can also be measured within a predetermined period.

In addition, the emotion amount to be measured can be switched within the event. For example, in the concert, the emotion amount to be measured can be switched depending on the type of music. As a result, it is possible to acquire the information on the emotion amount corresponding to various emotions.

In order to obtain a more accurate emotion transmission ability, it is preferable to eliminate the influence of the event itself. Regarding the emotion amount, the difference between the audiences may be captured by subtracting the average value calculated from the whole or a part of the venue.

In addition, in order to suppress the variation due to the magnitude of the emotional expression for each audience, it may be normalized by using the maximum value and the minimum value of the emotion amount throughout the event for each audience.

[Modification Example of Emotion Transmission Ability Estimation Device]

In the embodiments described above, the emotion transmission ability is defined by the leadership and the followership, but the emotion transmission ability can be defined by only one of the leadership or the followership. Further, the emotion transmission ability can be defined by adding other abilities. For example, an ability to cool emotion down can be added. The ability to cool emotion down can be obtained, for example, by a rate of decrease in the emotion amount per unit time.

Modification Example of Database Device

In the embodiments described above, the configuration has been adopted in which the audience is specified by the seat position and the user ID of the audience at the seat position, but a method of specifying the audience is not limited to this. For example, a configuration can be adopted in which each individual audience is specified by so-called face recognition by using the image obtained by imaging the audience. In this case, for example, a database for the face recognition that stores an individual's face in association with the user ID is prepared. In addition, the face of each audience is detected from the image obtained by imaging the audience, and the individual is specified by collating with the face image registered in the database. That is, the user ID is specified. As the image obtained by imaging the audience, for example, the image captured by the imaging unit of the emotion amount measurement device can be used. In addition, the images captured separately can be used.

System Configuration

In the embodiments described above, the configuration has been adopted in which the emotion transmission ability estimation device 100, the database device 200, and the placement decision device 300 are separate devices, but the devices can also be configured as one device. That is, these functions may be realized by one computer. The functions realized by the computer configuring this device can include the function of the measurement device body 30 of the emotion amount measurement device 10.

The hardware structure of the processing unit that executes various pieces of processing is realized by various processors. The various processors include the central processing unit (CPU) that is a general-purpose processor executing the program and functioning as the various processing units, a programmable logic device (PLD) that is a processor whose circuit configuration can be changed after manufacture, such as a field programmable gate array (FPGA), and a dedicated electric circuit that is a processor having a circuit configuration that is designed for exclusive use in order to execute specific processing, such as an application specific integrated circuit (ASIC). The program is synonymous with the software.

One processing unit may be configured by one of these various processors or may be configured by two or more processors of the same type or different types. For example, one processing unit may be configured by a plurality of FPGAs or a combination of the CPU and the FPGA. In addition, a plurality of the processing units may be configured by one processor. As an example of configuring a plurality of processing units with one processor, first, as represented by a computer such as a client or a server, there is a form in which one processor is configured by a combination of one or more CPUs and software, and the processor functions as a plurality of processing units. Second, as represented by a system on chip (SoC), there is a form in which a processor is used that realizes the functions of the entire system including a plurality of processing units with a single integrated circuit (IC) chip. In this way, the various processing units are configured by one or more of various processors described above as the hardware structures.

Explanation of References

1: information processing system
4: area in which audience is present (first area)
5: region in which emotion amount is equal to or more than threshold value in heat map
6: centroid of region
7: circle
8: audience
8$x$: audience
10: emotion amount measurement device
20: imaging unit
21: imaging apparatus
30: measurement device body
30A: image acquisition unit
30B: face detection unit
30C: emotion measurement unit
30D: selection unit
30E: emotion amount calculation unit
30F: emotion amount information output unit
31: CPU
34: HDD
35: operation unit
37: image input unit
38: communication unit
100: emotion transmission ability estimation device
100A: emotion amount information input unit
100B: heat map creation unit
100C: emotion transmission ability estimation unit
100D: emotion transmission ability information output unit
101: CPU
102: ROM
103: RAM
104: HDD
107: communication unit
200: database device
210: emotion transmission ability information input unit
212: attribute information input unit
214: database processing unit
216: data storage unit
300: placement decision device
310: venue information input unit
312: audience information input unit
314: emotion transmission ability information acquisition unit
316: placement decision unit
318: emotion transmission ability discrimination unit
320: appropriate person extraction unit
322: request reception unit
A: audience
B: audience
C: audience
D: audience
HM: heat map
S1 to S6: processing procedure until database is created
S11-S14: procedure of audience placement decision processing using customer database
r: radius of circle

What is claimed is:
1. An information processing system comprising:
a memory; and
a processor configured to:

capture a time series of images of each person of a plurality of people in a first area;

measure an index of emotion of each person of the plurality of people in the first area based on the time series of images;

create a heat map representing the measured index of emotion of each person of the plurality of people in the first area in association with a position of each person of the plurality of people in the first area;

estimate an emotion transmission ability of each person of the plurality of people in the first area based on the heat map;

register and store the estimated emotion transmission ability of each person of the plurality of people in the first area in the memory;

receive information on a target person to be placed in a second area;

acquire information on emotion transmission abilities of a plurality of registered people placed in the second area from the memory; and decide placement of the target person in the second area based on the information on the emotion transmission abilities of the plurality of registered people placed in the second area.

2. The information processing system according to claim 1, wherein the processor is further configured to:

for each person of the plurality of people in the first area,
measure emotion of the person in the first area, and
calculate the index of emotion of the person in the first area based on a measurement result of emotion of the person in the first area.

3. The information processing system according to claim 2, wherein the processor is further configured to, for each person of the plurality of people in the first area, calculate the index of emotion of the person in the first area based on the measurement result of emotion of the person in the first area as at least one of a level of emotion or amplitude of emotion of the person in the first area.

4. The information processing system according to claim 2, wherein the processor is further configured to:

for each person of the plurality of people in the first area,
detect a face of the person in the first area from the captured time series of images, and
measure emotion of the person in the first area based on an image of the detected face of the person in the first area.

5. The information processing system according to claim 2, wherein the processor is further configured to:

for each person of the plurality of people in the first area,
receive biological information of the person in the first area, and
calculate the index of emotion of the person in the first area based on the received biological information of the person in the first area.

6. The information processing system according to claim 2, wherein the processor is further configured to:

for each person of the plurality of people in the first area,
receive information on voice uttered by the person in the first area, and
calculate the index of emotion of the person in the first area based on the received information on the voice uttered by the person in the first area.

7. The information processing system according to claim 2, wherein the processor is further configured to:

for each person of the plurality of people in the first area,
receive information on vibration of the person in the first area, and
calculate the index of emotion of the person in the first area based on the received information of vibration of the person in the first area.

8. The information processing system according to claim 1, wherein the processor is further configured to estimate, as the emotion transmission ability, at least one of a first ability, which is an ability to give emotion to surroundings, or a second ability, which is an ability to accept emotion of surroundings.

9. The information processing system according to claim 1, wherein the processor is further configured to extract a region in which the index of emotion of the plurality of people in the first area is equal to or more than a threshold value from the map data, obtain a centroid of the extracted region, and estimate the first ability of each person of the plurality of people in the first area in the extracted region.

10. The information processing system according to claim 9, wherein the processor is further configured to calculate a sum of the indexes of emotion of all the plurality of people in the first area in the extracted region from the heat map, and estimate a degree of the ability of a person positioned at the centroid of the extracted region.

11. The information processing system according to claim 8, wherein the processor is further configured to, based on the heat map, obtain a sum of indexes of emotion of all the plurality of people in the first area positioned within a predetermined distance from a person in the first area for each person of the plurality of people in the first area.

12. The information processing system according to claim 8, wherein the processor is further configured to estimate the second ability of each person of the plurality of people in the first area based on the heat map.

13. The information processing system according to claim 12, wherein the processor is further configured to obtain a propagation rate of the index of emotion from the heat map, and estimate a degree of the second ability of the person in the first area.

14. The information processing system according to claim 1, wherein the processor is further configured to receive attribute information of each person of the plurality of people in the first area, and the memory further stores the received attribute information of each person of the plurality of people in the first area.

15. The information processing system according to claim 1, wherein the processor is further configured to estimate the emotion transmission ability of a person whose information is not stored in the memory, based on the estimated emotion transmission ability of each person of the plurality of people in the first area.

16. The information processing system according to claim 15,
wherein the processor is further configured to estimate the emotion transmission ability of the person whose information is not stored in the memory by using a discrimination model generated by machine learning.

17. The information processing system according to claim 16,
wherein the processor is further configured to estimate the emotion transmission ability of the person whose information is not stored in the memory by using the discrimination model generated by machine learning using the estimated emotion transmission ability of each person of the plurality of people in the first area stored in the memory.

18. The information processing system according to claim 1,
wherein the processor is further configured to, based on the information on the emotion transmission ability of each of the registered people placed in the second area, simulate a change of an index of emotion of the target person placed in the second area, obtain placement based on the index of emotion of the target person placed in the second area, and decide the placement of the target person in the second area, in the decision of the placement of the target person in the second area.

19. The information processing system according to claim 18,
wherein the processor is further configured to:
extract a person having a highest emotion transmission ability from among the plurality of registered people placed in the second area, and
decide the placement of the target person in the second area by adding the extracted person in the decision of the placement of the target person in the second area.

20. The information processing system according to claim 1,
wherein the processor is further configured to
receive a request for placement from the target person placed in the second area, and
decide the placement of the target person in the second area based on the request in the decision of the placement of the target person in the second area.

21. An information processing method comprising:
capturing a time series of images of each person of a plurality of people in a first area;
measuring an index of emotion of each person of the plurality of people in the first area based on the time series of images;
creating a heat map representing the measured index of emotion of each person of the plurality of people in the first area in association with a position of each person of the plurality of people in the first area;
estimating an emotion transmission ability of each person of the plurality of people in the first area based on the heat map;
registering and storing the estimated emotion transmission ability of each person of the plurality of people in the first area in a memory;
receiving information on a target person to be placed in a second area;
acquiring information on emotion transmission abilities of a plurality of registered people placed in the second area from the memory; and
deciding placement of the target person in the second area based on the information on the emotion transmission abilities of the plurality of registered people placed in the second area.

* * * * *